(12) United States Patent
Kim et al.

(10) Patent No.: US 12,116,597 B2
(45) Date of Patent: Oct. 15, 2024

(54) AUTOPHAGY AS A THERAPEUTIC TARGET FOR INTRACRANIAL ANEURYSM

(71) Applicant: THE BOARD OF REGENTS OF THE UNIVERSITY OF TEXAS SYSTEM, Austin, TX (US)

(72) Inventors: Dong H. Kim, Houston, TX (US); Yanning Rui, Houston, TX (US); Zhen Xu, Houston, TX (US); John Hagan, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/824,621

(22) Filed: May 25, 2022

(65) Prior Publication Data

US 2023/0270715 A1    Aug. 31, 2023

Related U.S. Application Data

(60) Provisional application No. 63/296,825, filed on Jan. 5, 2022, provisional application No. 63/296,817, filed on Jan. 5, 2022, provisional application No. 63/296,821, filed on Jan. 5, 2022, provisional application No. 63/296,820, filed on Jan. 5, 2022.

(51) Int. Cl.

| | | |
|---|---|---|
| *C12N 5/071* | (2010.01) | |
| *A61B 17/12* | (2006.01) | |
| *A61K 31/351* | (2006.01) | |
| *A61K 31/37* | (2006.01) | |
| *A61K 31/404* | (2006.01) | |
| *A61K 31/4706* | (2006.01) | |
| *A61K 31/496* | (2006.01) | |
| *A61K 31/5025* | (2006.01) | |
| *A61K 31/506* | (2006.01) | |
| *A61K 31/517* | (2006.01) | |
| *A61K 31/52* | (2006.01) | |
| *A61K 31/5377* | (2006.01) | |
| *A61K 31/55* | (2006.01) | |
| *A61K 38/10* | (2006.01) | |
| *A61P 9/00* | (2006.01) | |
| *A61P 9/10* | (2006.01) | |
| *C07K 14/495* | (2006.01) | |

(52) U.S. Cl.
CPC .......... *C12N 5/069* (2013.01); *A61B 17/1215* (2013.01); *A61K 31/351* (2013.01); *A61K 31/37* (2013.01); *A61K 31/404* (2013.01); *A61K 31/4706* (2013.01); *A61K 31/496* (2013.01); *A61K 31/5025* (2013.01); *A61K 31/506* (2013.01); *A61K 31/517* (2013.01); *A61K 31/52* (2013.01); *A61K 31/5377* (2013.01); *A61K 31/55* (2013.01); *A61K 38/10* (2013.01); *A61P 9/00* (2018.01); *A61P 9/10* (2018.01); *C07K 14/495* (2013.01); *C12N 2510/02* (2013.01)

(58) Field of Classification Search
None
See application file for complete search history.

(56) References Cited

FOREIGN PATENT DOCUMENTS

JP        2006528973        * 12/2006

OTHER PUBLICATIONS

Yu et al. (Sci Rep. Nov. 9, 2017;7(1):15208) (Year: 2017).*
Li et al. (CNS Neurosci Ther. Feb. 2019;25(2):233-244) (Year: 2019).*
Santiago-Sim et al. (Stroke. Dec. 2016 ; 47(12): 3005-3013) (Year: 2016).*
Lusini et al. (Future Cardiol. (2020) 16(5), 517-526) (Year: 2020).*
Yang et al. (Acta Pharmacol Sin. May 2013; 34(5): 625-635) (Year: 2013).*
Rui et al., Cell Physiol Biochem 2017;43:2200-2211 (Year: 2017).*
Xu, Z., et al., "Intracranial Aneurysms: Pathology, Genetics, and Molecular Mechanisms", NeuroMolecular Medicine (2019) 21:325-343.
Santiago-Sim, T., et al., "THSD1 (Thrombospondin Type 1 Domain Containing Protein 1) Mutation in the Pathogenesis of Intracranial Aneurysm and Subarachnoid Hemorrhage", Basic Sciences; downloaded from http://ahajournals.org by on Mar. 24, 2020.
Rui, Yan-Ning, et al., "The Intracranial Aneurysm Gene THSD1 Connects Endosome Dynamics to Nascent Focal Adhesion Assembly" Cell Physiol Biochem 2017; 43: 2200-2211.
Xu, Z., et al., "Precision Tagging: A Novel Seemless Protein Tagging System by Combinatorial Use of Type II and Type IIS Restriction Endonucleases", Biochemical and Biophysical Research Communications 490 (2017) 8-16.

* cited by examiner

*Primary Examiner* — Sergio Coffa
(74) *Attorney, Agent, or Firm* — Naira Simmons; Pierson Ferdinand LLP

(57) ABSTRACT

Disclosed here are uses of autophagy inhibitors for treating a subject at risk of suffering from an aneurysm. The present disclosure demonstrates that autophagy plays a role in THSD1-mediated focal adhesion stability and aneurysm formation and characterizes molecular targets for therapeutic intervention.

16 Claims, 11 Drawing Sheets

Patient-identified THSD1 variants. All variants are highlighted in red.
SP: signal peptide; TSP1: thrombospondin type 1 domain;
TM: transmembrane

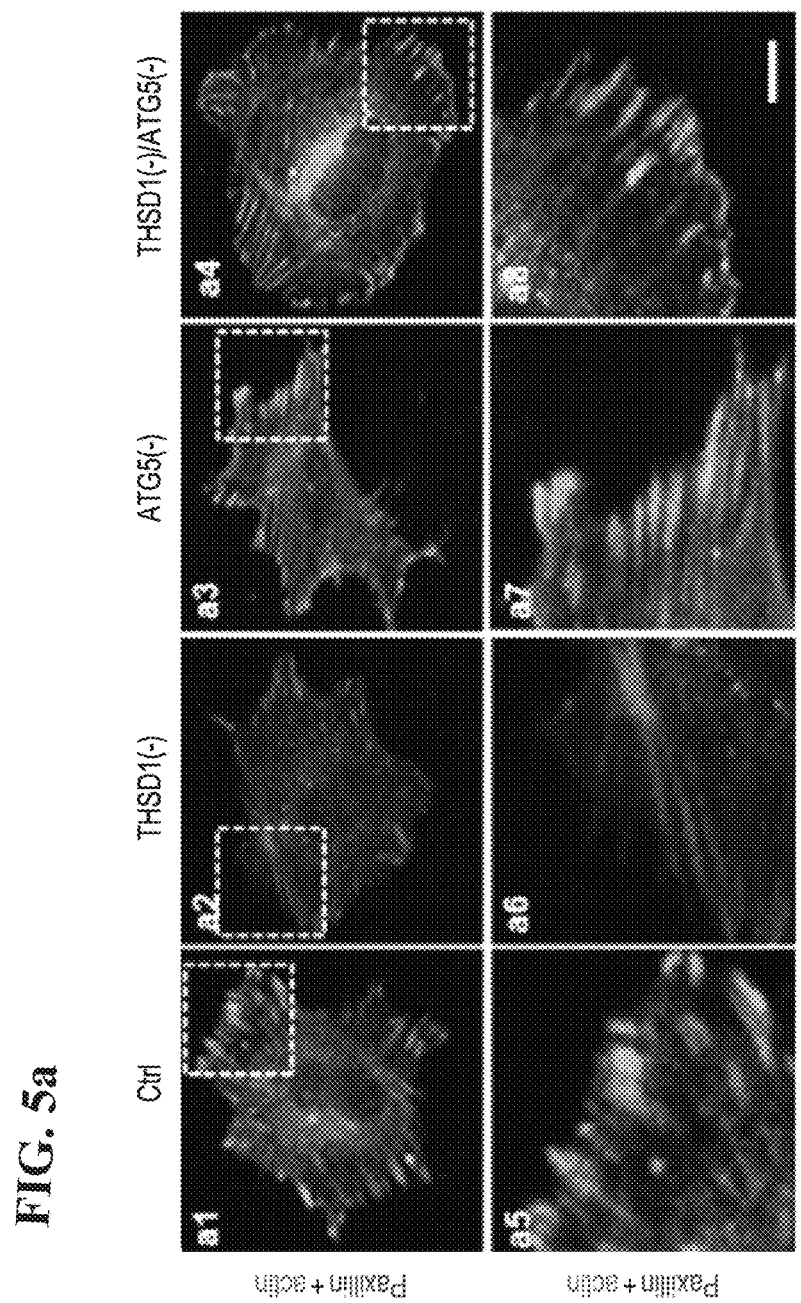

AUTOPHAGY AS A THERAPEUTIC TARGET FOR INTRACRANIAL ANEURYSM

CROSS-REFERENCE

The present application claims priority to U.S. Provisional Application Ser. No. 63/296,820, filed Jan. 5, 2022; U.S. Provisional Application Ser. No. 63/296,817, filed Jan. 5, 2022; U.S. Provisional Application Ser. No. 63/296,821, filed Jan. 5, 2022; and U.S. Provisional Application Ser. No. 63/296,825, filed Jan. 5, 2022, the contents of each being hereby incorporated by reference in their entirety.

FIELD OF THE INVENTION

The present disclosure relates to the characterization of molecular targets for treating intracranial aneurysms (IA). Intracranial aneurysm (IA) is a cerebrovascular disease that predominantly occurs in the cerebral artery and is characterized by pathologic dilatation of blood vessels. Each intracranial aneurysm (IA) is a weakened area in a cerebral artery wall that leads to abnormal dilatation and rupture causing subarachnoid hemorrhage (SAH), a major cause of hemorrhagic stroke. A rupture of IA induces a subarachnoid hemorrhage (SAH), a type of hemorrhagic stroke that frequently leads to death or severe disability. Due to early age of onset and high mortality, SAH accounts for >25% of years lost for all stroke victims under the age of 65 years. Despite treatment advances, SAH mortality rate is 40% and only half of survivors return to independent life.

There is a critical unmet need for understanding the genetic and molecular basis for IA to improve clinical outcomes through early therapeutic intervention.

SUMMARY

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

In some aspects, the present disclosure demonstrates that autophagy plays a role in THSD1-mediated focal adhesion stability and aneurysm formation. Briefly, the present disclosure provides that THSD1 can be a new, endothelial-specific, mechanosensory protein that regulates the autophagy pathway.

In some aspects, the disclosure provides a therapeutic method to treat a subject at risk of suffering from an aneurysm comprised of administering to said subject a therapeutically effective dose of an autophagy inhibitor. The autophagy inhibitor can be a phagophore inhibitor, a autophagosome inhibitor, an autolysosome inhibitor, or an inhibitor of the autophagosome-lysosome fusion. In some cases, the autophagy inhibitor is selected from the group consisting of wortmannin, chloroquine, clomipramine, 3-Methyladenine, Bafilomycin A1, Pepstatin A, and Pepstatin E-64-d. The aneurysm can be any aneurysm, and in some cases it is an intracranial aneurysm in others it is an aortic aneurysm. In some cases, the subject carries a variant affecting the expression of a Thrombospondin Type 1 Domain Containing 1 (THSD1) gene. The variant can be in a coding region, in a control sequence, or in a non-coding region of the Thrombospondin Type 1 Domain Containing 1 (THSD1) gene. In some cases the variant has a single codon substitution in at least one THSD1 allele relative to NCBI Reference Sequence: NP_061146.1. In specific cases, the single codon substitution is L5F, R460W, E466G, G600E, P639L. T653I, or S775P. In some instances the therapeutically effective dose of the autophagy inhibitor is administered systemically, and the systemic administration can include, but it is not limited to: (i) intravenous; (ii) intra-arterial; (iii) subcutaneous; or (iv) intraperitoneal. In other cases, the therapeutically effective dose of the autophagy inhibitor is administered locally. The local administration can include, but is not limited to, (i) intracranial; (ii) intra-ocular; (iii) intra-nasal; (iv) intrathecal or (v) intra-vascular. In preferred instances the subject is a human.

In some aspects the disclosure describes an autophagy inhibitor for use in a method of treating an aneurysm in a subject. The disclosure provides for a use of an autophagy inhibitor in the manufacture of a medicament for the treatment of an aneurysm, such as intracranial aneurysm (IA) or aortic aneurysm (AA). The disclosure provides for a use of an autophagy inhibitor for the treatment of an aneurysm, such as intracranial aneurysm (IA) or aortic aneurysm (AA). The autophagy inhibitor can be a phagophore inhibitor, an autophagosome inhibitor, an autolysosome inhibitor, or an inhibitor that blocks the autophagosome-lysosome fusion. In some instances the autophagy inhibitor is selected from the group consisting of wortmannin, chloroquine, clomipramine, 3-Methyladenine, Bafilomycin A1, Pepstatin A, or Pepstatin E-64-d. The aneurysm can be an intracranial aneurysm or an aortic aneurysm. The subject can carry a variant affecting the expression of a Thrombospondin Type 1 Domain Containing 1 (THSD1) gene. Such variants can be in a coding region, in a control sequence, or in a non-coding region of the Thrombospondin Type 1 Domain Containing 1 (THSD1) gene. In some cases, the variant in the THSD1 gene is a single codon substitution in at least one THSD1 allele, such as L5F, R460W, E466G, G600E. P639L, T653I, or S775P. In some instances the therapeutically effective dose of the autophagy inhibitor is administered systemically, and the systemic administration can include, but it is not limited to: (i) intravenous; (ii) intra-arterial; (iii) subcutaneous; or (iv) intraperitoneal. In other cases, the therapeutically effective dose of the autophagy inhibitor is administered locally. The local administration can include, but is not limited to, (i) intracranial; (ii) intra-ocular; (iii) intra-nasal; (iv) intrathecal or (v) intra-vascular. In preferred instances the subject is a human.

The present disclosure also provides for a kit(s) comprising any one of the autophagy inhibitors described herein and instructions for use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features and advantages of the present invention will be more fully understood from the following detailed description of illustrative embodiments taken in conjunction with the accompanying drawings in which:

FIG. 1A illustrates Intracranial Aneurysm (IA) affected (black), aortic aneurysm (AA) affected (half black), unaffected individuals >45 (white), and individuals with unknown/unclear status (gray symbols).

FIG. 5a through FIG. 5b (FIG. 5a-5b) are experimental results depicting that autophagy inhibition rescues focal adhesion defects in THSD1-deficient endothelial cells.

Figure 9A:
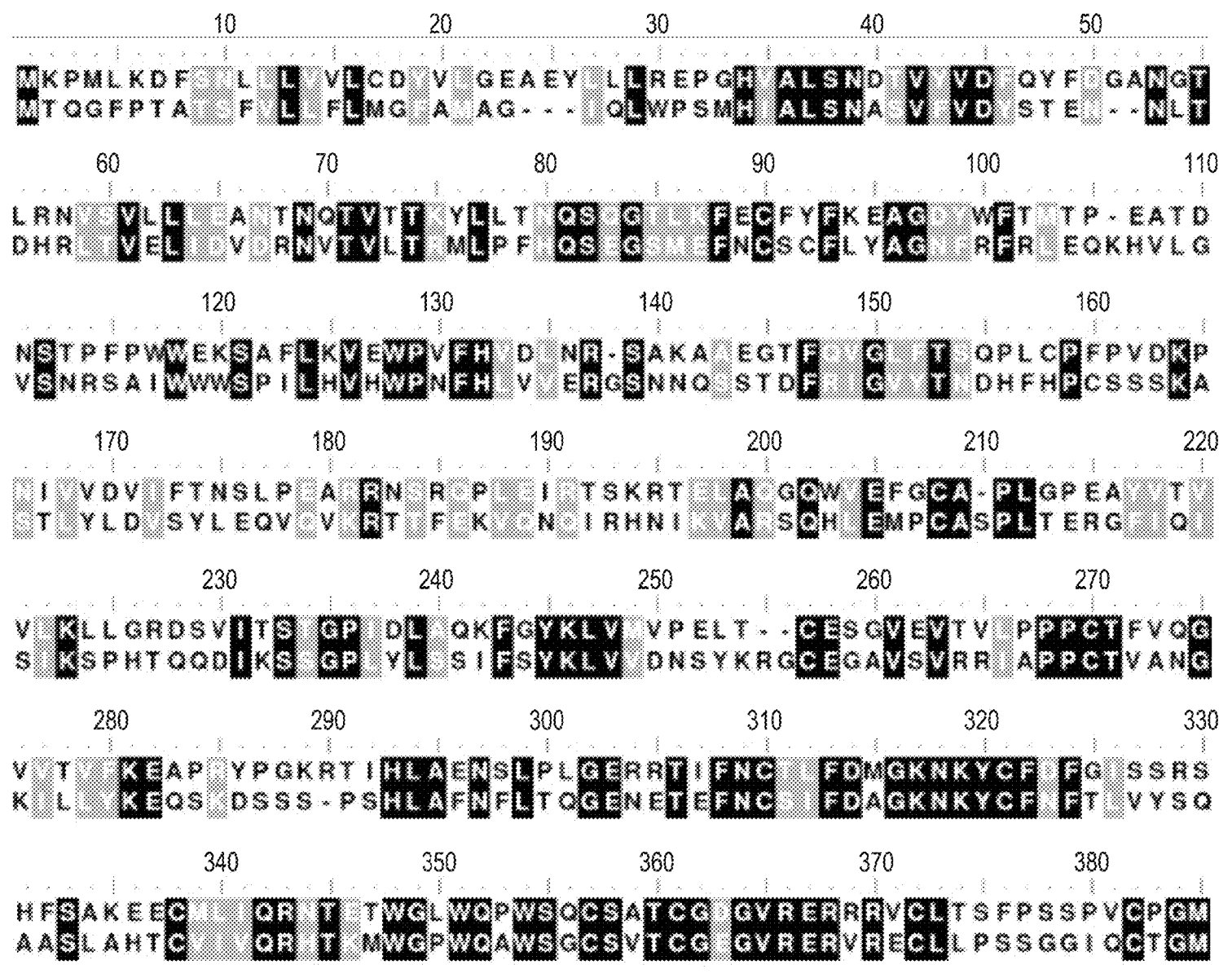
Figure 9B:
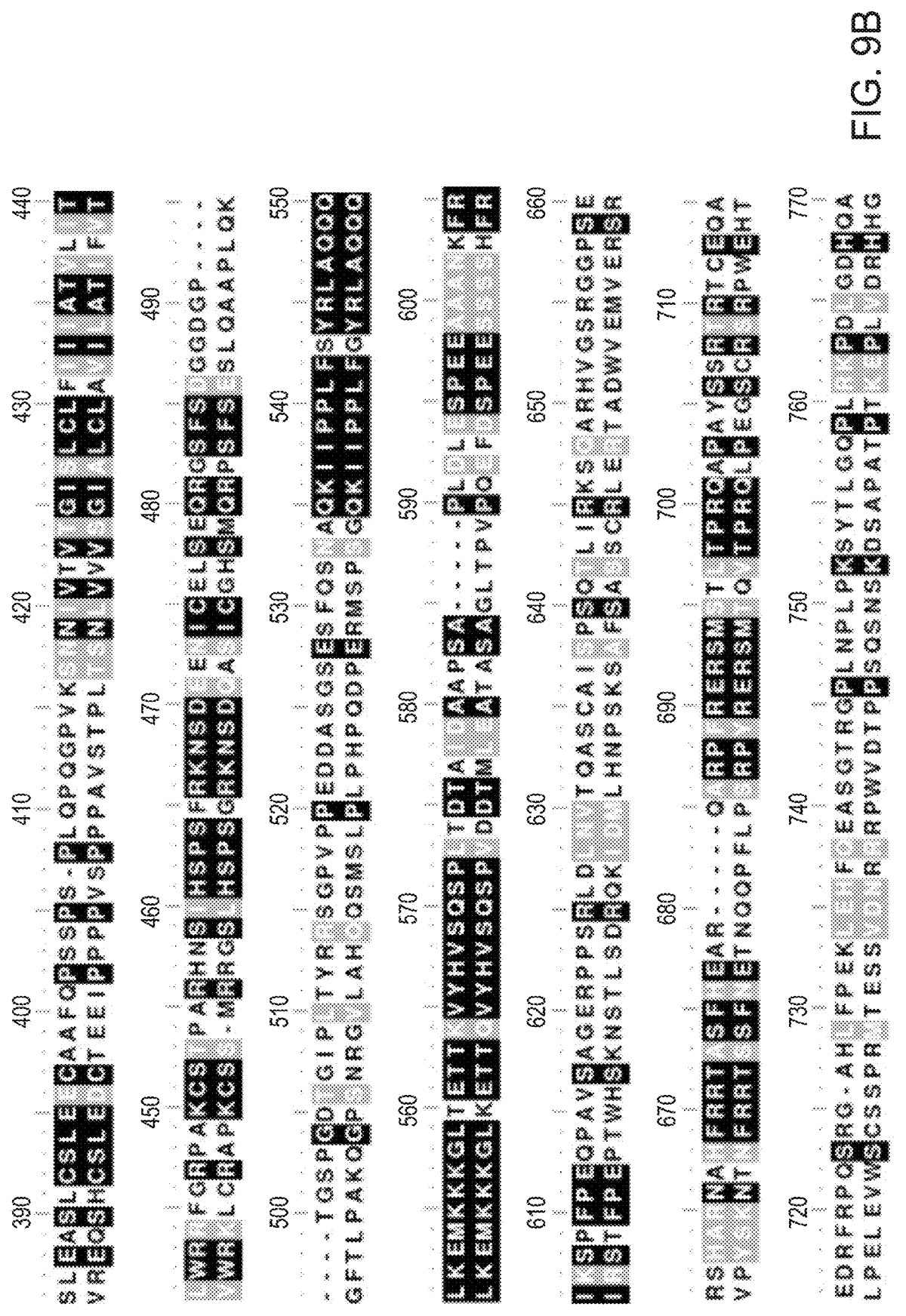

FIG. 9A through FIG. 9C are protein alignments between human and zebrafish THSD1.

It should be understood that the drawings are not necessarily to scale, and that like reference numbers refer to like features.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTIONS

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The rupture of an intracranial aneurysm frequently causes a subarachnoid hemorrhage (SAH), a type of stroke characterized by high morbidity and mortality. Specifically, the present disclosure demonstrates with data from three large IA/SAH families with at least 4 affected individuals where whole exome sequencing has been performed to identify rare variants that segregate with disease. For each family, whole exome sequencing has been performed on at least 15 family members, irrespective of their IA status.

Figure 1A:
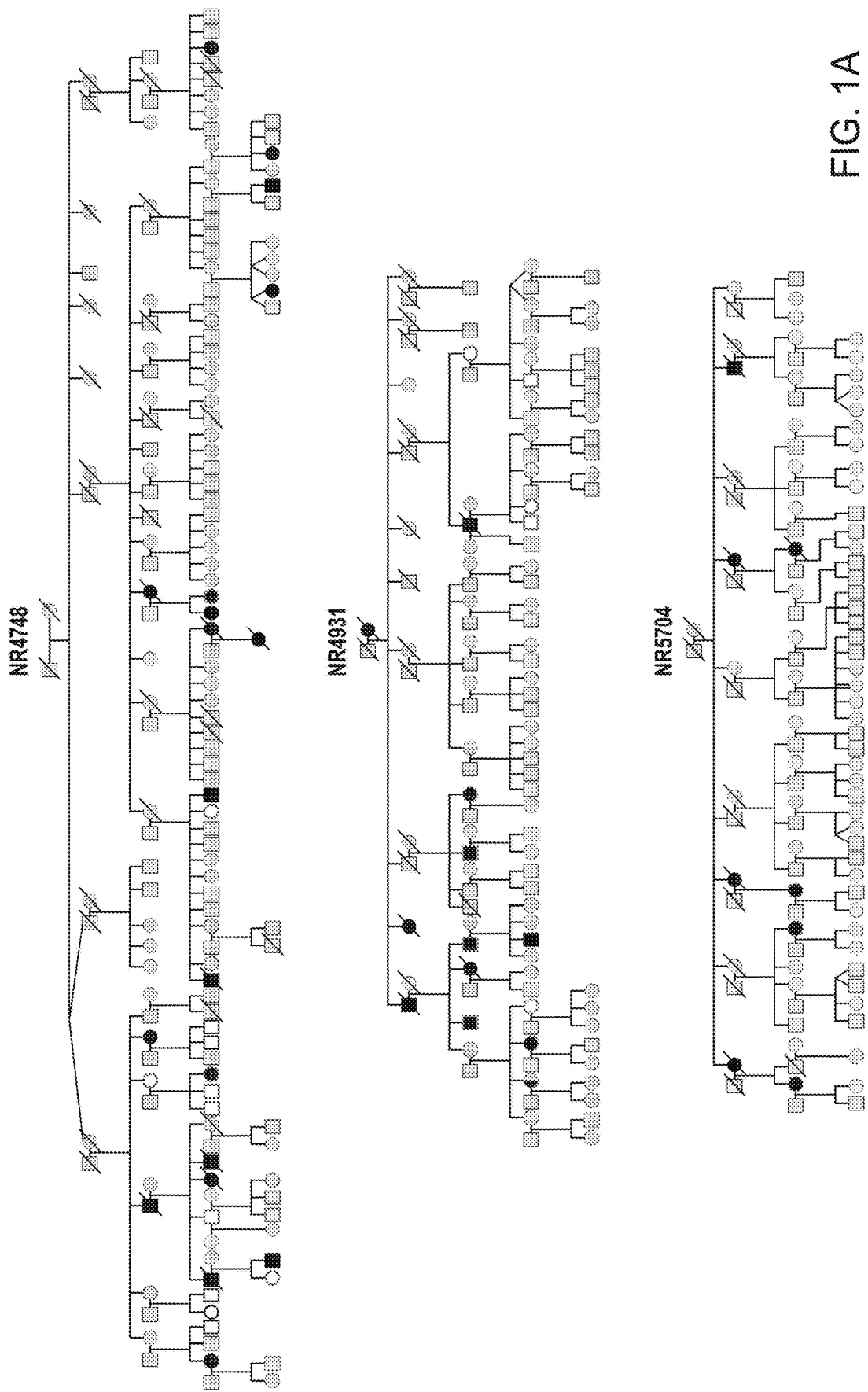
FIG. 1A (FIG. 1A) illustrates simplified pedigrees of three IA families (NR4748, NR4931, and NR5704). Specifically.

Previously, it has been reported that deleterious Thrombospondin-type 1 domain-containing protein 1 (THSD1) rare variants caused disease in both familial and sporadic cases with supporting evidence from animal models. Of note, whole exome sequencing of large IA families identified (some members of the affected family are shown in the pedigree of FIG. 1A) a THSD1 nonsense mutation that segregated in all nine (9) affected and was absent in 13 unaffected family members. It was further discovered that eight (8) THSD1 rare missense variants in 507 unrelated patients/probands where each perturbed THSD1 cell adhesion activity.

These rare variants were highly enriched in case-control studies in comparison to ethnically matched controls. It was found that Thsd1 loss-of-function leads to brain hemorrhage and premature death in both zebrafish and mice. Further, Thsd1 heterozygous and null mice developed IA and suffered SAH. The study further demonstrated that THSD1 is highly expressed in endothelial cells of the cerebrovasculature, is important for cell adhesion, promotes nascent focal adhesion assembly via Talin interactions, and potentially regulates downstream signaling. For further description of this work see. Z. Xu, D. Kim, et al., NeuroMolecular Medicine (2019) 21:325-343; T. Santiago-Sim, D. Kim, et al., Stroke. 2016; 47:3005-3013. DOI: 10.1161/STROKEAHA.116.014161); Yan-Ning Rui and D. Kim, et al., Cell Physiol Biochem 2017; 43:2200-2211; each of which incorporated by reference in their entireties). However the study did not provide any insights on the THSD1 molecular pathways.

Figure 1B:
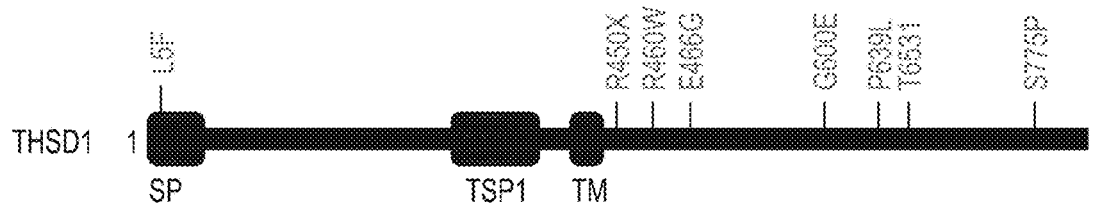
FIG. 1B (FIG. 1B) depicts patient-identified THSD1 variants identified in the pedigrees of the families from FIG. 1B. The black bar represents the 853 amino acids of the WT version of the THSD1 gene. The diagram lists 8 variants found in patients affected by IA and AA, namely L5F, R450X, R460W, E466G, G600E, P639L, T653I, S775P. The back boxes illustrate the relative position of the signal peptide (SP), thrombospondin type 1 domain (TSP1), and transmembrane (TM) domains of THSD1.
Figure 2:
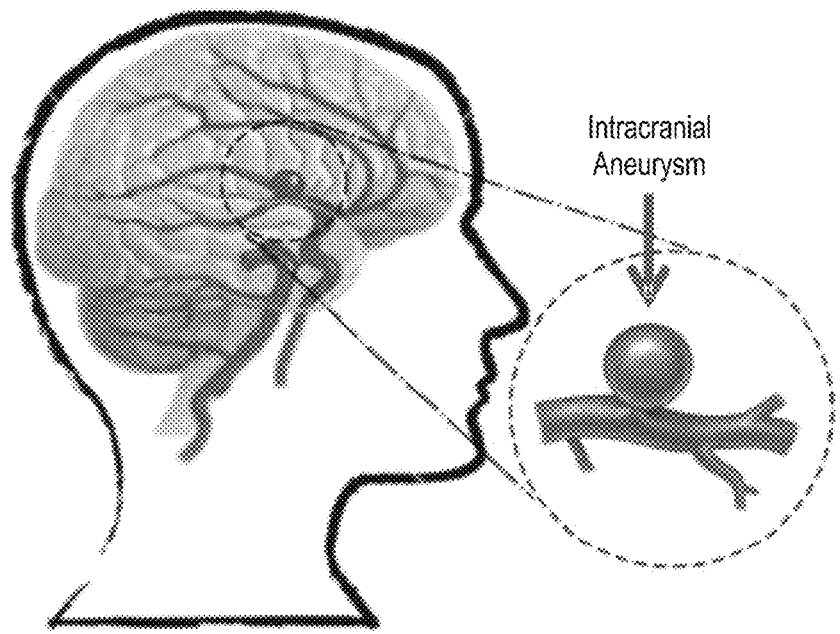
FIG. 2 (FIG. 2) is a drawing depicting an intracranial aneurysm. An intracranial aneurysm, also known as a brain aneurysm, is a cerebrovascular disorder in which weakness in the wall of a cerebral artery or vein causes a localized dilation or ballooning of the blood vessel.

To further study the role of THSD1 in IA/SAH, additional analysis of whole exome sequencing of the IA families described in FIG. 1 was conducted. The detailed analysis identified a THSD1 nonsense mutation that segregated in all 9 affected and was absent in 13 unaffected family members. Notably, the exome sequencing analysis uncovered multiple signaling pathways that appeared to be affected by THSD1 expression: Integrin, Src, PI3/AKT/mTor, and Rho signaling that are functionally linked to Focal Adhesion Kinase (FAK) signaling as well as TGFβ signaling (see Table 1, discussed in Example 1). The present disclosure contemplates that THSD1 regulated genes may contribute to IA pathogenesis and that modulating their function may be beneficial as an IA treatment or in other diseases with aberrant THSD1 expression.

The present disclosure considered the differentially expressed genes and characterized autophagy pathways as contributors to IA development and potential targets for therapy. The present disclosure also contemplates that mutations in genes other than THSD1 that affect the autophagy pathway could render a subject at risk of suffering an IA. The present disclosure characterizes in detail the autophagy pathway as a novel molecular target for the treatment of subjects at risk of developing an aneurysm.

In some aspects, the present disclosure provides the molecular characterization of autophagy in the IA pathology.

Autophagy is a catabolic process that degrades intracellular cargos. The autophagosome, a double membrane-bound vesicle with microtubule-associated protein 1A/1B-light chain 3 (LC3) protein associated on both sides, engulfs cytoplasmic constituents and later fuses with lysosome for degradation. In comparison to starvation-induced bulk autophagy, selective autophagy plays an important role in controlling organelle homeostasis. NBR1-mediated or Src-mediated selective autophagy were found to degrade FA via distinct mechanisms. NBR1 as a cargo receptor bridges LC3 to paxillin, a universal marker for FA, whereas SRC kinase promotes the direct interaction of LC3 and paxillin in a phosphorylation-dependent manner. However, the upstream signaling that determines the temporospatial degradation of FA remained unclear. The present disclosure considered different stages of autophagy pathway as potentially providing therapeutic targets for treatment of a genetic aneurysm in subjects at risk.

In some aspects, the present disclosure demonstrates that THSD1, as a transmembrane protein, is the upstream regulator of the selective autophagy cascade in endothelial cells. The disclosure contemplates that the THSD1-autophagy-FA axis regulates cerebrovascular integrity, and this is impaired in subjects that are prone or at risk of suffering an aneurysm particularly an intracranial aneurysm.

In some aspects, the present disclosure provides a method to treat a subject at risk of suffering from an aneurysm comprised of administering to said subject a therapeutically effective dose of a compound that modulates autophagy biogenesis. Examples of such compounds considered by the disclosure include: vertepofin, chloroquine, and/or clomipramine. Vertepofin was reported to inhibit autophagosome biogenesis, while chloroquine and clomipramine were reported to inhibit autophagosome-lysosome fusion. Autophagosome biogenesis and autophagosome-lysosome fusion are two sequential steps in autophagy. In many instances the subject carries a variant affecting the expression of a Thrombospondin Type 1 Domain Containing 1 (THSD1) gene. The variant can be in a coding region of the THSD1 gene, in a control sequence of a non-coding region of the THSD1 gene, or in any other suitable region. In some instances, the variant in the THSD1 gene is a single codon substitution in at least one THSD1 allele, such as the exemplary variants identified and described in FIG. 1B, which include single codon substitutions at codon L5F, R460W, E466G, G600E, P639L, T653I, S775P.

Methods of Treating Intracranial Aneurysms

The methods, compositions, and uses of this disclosure may comprise a treatment method to arrest, reverse, or ameliorate an aneurysm, e.g., an intracranial aneurysm. In some cases, the therapeutic effect is achieved by administrating a therapeutically-effective dose of a autophagy inhibitor.

Wherein an autophagy inhibitor is utilized, the inhibitor may be of any suitable kind as long as it leads to autophagy inhibition. For instance, the inhibitor may block a phagophore (see FIG. 3; illustrating 3MA as an exemplary inhibitor of a phagophore), it may block an autophagosome (see FIG. 3; illustrating 3MA as an exemplary inhibitor of an autophagosome), or it may block an autolysosome (see FIG. 3; illustrating P/E—i.e., Pepstatin A and E-64-d—, as an exemplary inhibitors of an autophagosome).

The treatment may comprise treating a subject (e.g. a patient at risk of having an intracranial aneurysm due to the presence of a THSD1 genetic variant or an animal with a similar genetic variant). The disease may be a weakness in a blood vessel in the brain that balloons and fills with blood, for example, a brain aneurysm (also called a cerebral aneurysm or an intracranial aneurysm) is a ballooning arising from a weakened area in the wall of a blood vessel in the brain. The subject may be a human.

Treatment may be provided to the subject before clinical onset of disease. For instance, in specific cases, treatment may be provided upon the identification of a THSD1 variant in a subject, before the onset of a disease. Treatment may be provided to the subject after clinical onset of disease. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment may also include treating a human in a clinical trial. Because of the genetic aspect of IA, treatment may be provided through the lifetime of a subject that is afflicted with a THSD1 variant that may lead to subarachnoid hemorrhage. In some aspects, treatment will be prescribed to prevent IA in a subject that carries a THSD1 variant associated with IA.

A treatment can comprise administering to a subject a pharmaceutical composition, such as one or more of the pharmaceutical compositions described throughout the disclosure. A treatment can comprise modulating the levels of autophagy in vivo. A treatment may comprise administering a suitable level of an autophagy inhibitor for reducing bulge's in the wall of a blood vessel and preventing Subarachnoid hemorrhage.

Further, there are many risk factors for the development of intracranial aneurysms, both inherited and acquired. Females are more prone to aneurysm rupture, with SAH times more common in women. The prevalence of aneurysms is increased in certain genetic diseases; the classic example is autosomal dominant polycystic kidney disease (ADPKD), but other diseases such as Ehlers-Danlos syndrome, neurofibromatosis, a1-antitrypsin deficiency also demonstrate a link.

In ADPKD, 10% to 15% of patients develop intracranial aneurysms. Marfan's Syndrome was once thought to be linked to intracranial aneurysm formation, but recent evidence suggests that this may not be true. Aneurysms also run in families in the absence of an identified genetic disorder, with a prevalence of 7% to 20% in first or second degree relatives of patients who have suffered a SAH. FIG. 1A discloses a large family with variants in the THSD1 gene that have been causally linked to IA.

Autophagy Inhibitors

The methods, compositions, and uses of this disclosure may comprise a treatment method to prevent, arrest, reverse, or ameliorate an intracranial aneurysm. In some cases, the therapeutic effect is achieved by administrating a therapeutically-effective dose of a autophagy inhibitor.

Autophagy is a conserved lysosomal-dependent catabolic process that maintains the cellular homeostasis by recycling misfolded proteins and damaged organelles. It involves a series of ordered events (initiation, nucleation, elongation, lysosomal fusion and degradation) that are tightly regulated/controlled by diverse cell signals and stress. Autophagy begins with the nucleation of phagophores, which then expand to give rise to the double-membrane autophagosomes. Autophagosomes ultimately fuse with lysosomes, where the cytosolic cargoes are degraded. How the phagophore is generated and grows into a sealed autophagosome is still not clear in detail, but inhibitors of each step have been identified.

A number of therapeutics exist that modulate the various stages of autophagy initiation (e.g., ULK kinase inhibitors), nucleation (e.g., Vps34 inhibitors), elongation (e.g., ATG4 inhibitors), phagophore domain (e.g., ATG5), and lysosome fusion (e.g., chloroquine, hydroxyl chloroquine, etc.). See FIG. 3 for an schematic of exemplary stages. Also a number of small molecules reported to induce autophagy by targeting mammalian target of rapamycin (e.g., rapamycin analogs) or adenosine 5'-monophosphate-activated protein kinase (e.g., sulforaphane). Thus, many potential therapeutic targets exist in the autophagy pathway that could be harnessed for developing new therapies that can be used to prevent aneurysms in individuals carrying genetic mutations known to lead to aneurysms. See, e.g., the individuals from FIG. 1A.

In some embodiments, an intracranial aneurysm is susceptible to treatment with an autophagy inhibitor of TABLE 1. Non-limiting examples of autophagy inhibitors include wortmannin, chloroquine and clomipramine. Vertepofin was reported to inhibit autophagosome biogenesis, while chloroquine and clomipramine were reported to inhibit autophagosome-lysosome fusion. Autophagosome biogenesis and autophagosome-lysosome fusion are two sequential steps in autophagy. A more comprehensive list of autophagy inhibitors include:

TABLE 1

Exemplary Autophagy Inhibitors

| Product Name | Activity |
|---|---|
| AS 1842856 | Potent and selective Foxo1 inhibitor; suppresses autophagy |
| Autophinib | Potent VPS34 inhibitor |
| Azithromycin | Autophagy inhibitor; antibiotic |
| Bafilomycin A1 | H+-ATPase (vacuolar) inhibitor; also inhibits autophagy |
| (±)-Bay K 8644 | L-type Ca2+ channel activator; inhibits autophagy |
| Chloroquine diphosphate | Inhibits apoptosis and autophagy |
| Clomipramine | Inhibits autophagosome-lysosome fusion |
| Concanamycin A | H+-ATPase (vacuolar) inhibitor |
| DBeQ | Selective p97 ATPase inhibitor; blocks autophagosome maturation |
| Pepstatin E 64d | Cathepsin inhibitor; interferes with autolysosomal digestion |
| Edaravone | Autophagy inhibitor; also anti-ischemic and antioxidant |
| GW 4064 | Selective farnesoid X receptor (FXR) agonist; suppresses autophagy in nutrient-deprived hepatocytes |
| Hydroxychloroquine sulfate | Autophagy inhibitor; also TLR9 inhibitor |
| LY 294002 hydrochloride | Prototypical PI 3-kinase inhibitor; inhibits autophagic sequestration |
| Mdivi 1 | Autophagy inhibitor; also selective dynamin inhibitor |
| 3-Methyladenine | Class III PI 3-kinase inhibitor; also inhibits autophagy |
| ML 240 | ATP-competitive inhibitor of p97 ATPase; impairs autophagosome maturation |
| MRT 67307 dihydrochloride | Autophagy inhibitor; also salt inducible kinase (SIK) inhibitor |
| MRT 68601 hydrochloride | Potent TBK1 inhibitor; also inhibits autophagy |
| MRT 68921 dihydrochloride | Autophagy inhibitor; potent ULK inhibitor |
| NMS 873 | Potent and selective p97 ATPase (VCP) allosteric inhibitor |

TABLE 1-continued

Exemplary Autophagy Inhibitors

| Product Name | Activity |
|---|---|
| Nocodazole | Microtubule inhibitor; inhibits autophagosome-lysosome fusion |
| Pepstatin A | Protease inhibitor; interferes with autolysosomal digestion |
| Spautin 1 | Inhibits autophagy; USP10 and USP13 inhibitor |
| Taxol | Promotes assembly and inhibits disassembly of microtubules |
| Vertepofin | Inhibits autophagosome biogenesis |
| Vinblastine sulfate | Disrupts microtubules; inhibits autophagosome maturation |
| Wortmannin | Potent, irreversible inhibitor of PI 3-kinase. Also inhibitor of PLK1 |
| Xanthohumol | p97 ATPase (VCP) inhibitor; impairs autophagosome maturation |

Definitions

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Furthermore, terms such as "first," "second," "third," etc., merely identify one of a number of steps, components, functions, and/or points of reference as disclosed herein, and likewise do not necessarily limit embodiments of the present disclosure to any particular configuration or orientation.

Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants.

As used in the specification and claims of this application, the term "administering" includes any method which is effective to result in delivery of an autophagy inhibitor to the subject.

As used in this specification, the term "aneurysm" refers to broad classes of aneurysm, including aneurysms: abdominal aortic, thoracic aortic, and cerebral.

As used in this specification, the term "cerebral aneurysm" or "intracranial aneurysm" (also known as a brain aneurysm) is a weak or thin spot on an artery in the brain that balloons or bulges out and fills with blood. The bulging aneurysm can put pressure on the nerves or brain tissue. It may also burst or rupture, spilling blood into the surrounding tissue (called a hemorrhage). An unruptured aneurysm usually causes no symptoms. A key symptom of a ruptured aneurysm is a sudden, severe headache. Treatments for an unruptured aneurysm include medications to control blood pressure and procedures to prevent a future rupture.

As used in this specification, the term "abdominal aortic" aneurysm (AAA) is a bulge or swelling in the aorta, the main blood vessel that runs from the heart down through the chest and tummy. An AAA can be dangerous if it is not spotted early on. It can get bigger over time and could burst (rupture), causing life-threatening bleeding.

As used in this specification, the term "abdominal aortic" aneurysm (AAA) is a bulge or swelling in the aorta, the main blood vessel that runs from the heart down through the chest and tummy. An AAA can be dangerous if it is not spotted early on. It can get bigger over time and could burst (rupture), causing life-threatening bleeding.

As used in this specification, the term "thoracic aortic" aneurysm is an abnormal widening or ballooning of a portion of an artery due to weakness in the wall of the blood vessel. A thoracic aortic aneurysm occurs in the part of the body's largest artery (the aorta) that passes through the chest.

As used in the specification and claims of this application, the term "at risk" or more specifically a "subject at risk of developing an intracranial aneurysm" is a subject afflicted with a genetic variant, e.g., THSD1 variant, that causes the subarachnoid hemorrhage seen when an aneurysm ruptures.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

EMBODIMENTS

EMBODIMENT 1. A method for treating a subject at risk of suffering from an aneurysm comprised of administering to said subject a therapeutically effective dose of an autophagy inhibitor.

EMBODIMENT 2. The method of embodiment 1, wherein the autophagy inhibitor is a phagophore inhibitor.

EMBODIMENT 3. The method of embodiment 1, wherein the autophagy inhibitor is a autophagosome inhibitor.

EMBODIMENT 4. The method of embodiment 1, wherein the autophagy inhibitor blocks the autophagosome-lysosome fusion.

EMBODIMENT 5. The method of embodiment 1, wherein the autophagy inhibitor is an autolysosome inhibitor.

EMBODIMENT 6. The method of embodiment 1, wherein the autophagy inhibitor is selected from the group consisting of wortmannin, chloroquine, clomipramine, 3-Methyladenine, Bafilomycin A1, Pepstatin A, and Pepstatin E-64-d.

EMBODIMENT 7. The method of embodiment 6, wherein the autophagy inhibitor is wortmannin.

EMBODIMENT 8. The method of embodiment 6, wherein the autophagy inhibitor is chloroquine.

EMBODIMENT 9. The method of embodiment 6, wherein the autophagy inhibitor is clomipramine.

EMBODIMENT 10. The method of embodiment 6, wherein the autophagy inhibitor is 3-Methyladenine.

EMBODIMENT 11. The method of embodiment 6, wherein the autophagy inhibitor is Bafilomycin A1.

EMBODIMENT 12. The method of embodiment 6, wherein the autophagy inhibitor is Pepstatin A.

EMBODIMENT 13. The method of embodiment 6, wherein the autophagy inhibitor is Pepstatin E-64-d.

EMBODIMENT 14. The method of embodiment 1, wherein the aneurysm is an intracranial aneurysm.

EMBODIMENT 15. The method of embodiment 1, wherein the aneurysm is an aortic aneurysm.

EMBODIMENT 16. The method of embodiment 1, wherein the subject carries a variant affecting the expression of a Thrombospondin Type 1 Domain Containing 1 (THSD1) gene.

EMBODIMENT 17. The method of embodiment 16, wherein the variant is in a coding region of the Thrombospondin Type 1 Domain Containing 1 (THSD1) gene.

EMBODIMENT 18. The method of embodiment 16, wherein the variant is in a control sequence of a non-coding region of the Thrombospondin Type 1 Domain Containing 1 (THSD1) gene.

EMBODIMENT 19. The method of embodiment 1, wherein the variant in the THSD1 gene is a single codon substitution in at least one THSD1 allele.

EMBODIMENT 20. The method of embodiment 1, wherein the single codon substitution is L5F, R460W, E466G, G600E, P639L, T653I, or S775P.

EMBODIMENT 21. The method of embodiment 1, wherein the therapeutically effective dose of the autophagy inhibitor is administered systemically.

EMBODIMENT 22. The method of embodiment 21, wherein systemic administration includes, but is not limited to: (i) intravenous; (ii) intra-arterial; (iii) subcutaneous; or (iv) intraperitoneal.

EMBODIMENT 23. The method of embodiment 1, wherein the therapeutically effective dose of the autophagy inhibitor is administered locally.

EMBODIMENT 24. The method of embodiment 23, wherein local administration includes, but is not limited to, (i) intracranial; (ii) intra-ocular; (iii) intra-nasal; (iv) intrathecal or (v) intra-vascular.

EMBODIMENT 25. The method of embodiment 1, wherein the subject is a human.

EMBODIMENT 26. An autophagy inhibitor for use in a method of treating an aneurysm in a subject.

EMBODIMENT 27. The autophagy inhibitor of embodiment 26, wherein the autophagy inhibitor is a phagophore inhibitor.

EMBODIMENT 28. The autophagy inhibitor of embodiment 26, wherein the autophagy inhibitor is an autophagosome inhibitor.

EMBODIMENT 29. The autophagy inhibitor of embodiment 26, wherein the autophagy inhibitor is an autolysosome inhibitor.

EMBODIMENT 30. The autophagy inhibitor of embodiment 26, wherein the autophagy inhibitor blocks the autophagosome-lysosome fusion.

EMBODIMENT 31. The autophagy inhibitor of embodiment 26, wherein the autophagy inhibitor is selected from the group consisting of wortmannin, chloroquine, clomipramine, 3-Methyladenine, Bafilomycin A1, Pepstatin A, or Pepstatin E-64-d.

EMBODIMENT 32. The autophagy inhibitor of embodiment 31, wherein the autophagy inhibitor is wortmannin.

EMBODIMENT 33. The autophagy inhibitor of embodiment 31, wherein the autophagy inhibitor is chloroquine.

EMBODIMENT 34. The autophagy inhibitor of embodiment 31, wherein the autophagy inhibitor is clomipramine.

EMBODIMENT 35. The autophagy inhibitor of embodiment 31, wherein the autophagy inhibitor is 3-Methyladenine.

EMBODIMENT 36. The autophagy inhibitor of embodiment 31, wherein the autophagy inhibitor is Bafilomycin A1.

EMBODIMENT 37. The autophagy inhibitor of embodiment 31, wherein the autophagy inhibitor is Pepstatin A.

EMBODIMENT 38. The autophagy inhibitor of embodiment 31, wherein the autophagy inhibitor is Pepstatin E-64-d.

EMBODIMENT 39. The autophagy inhibitor of embodiment 26, wherein the aneurysm is an intracranial aneurysm.

EMBODIMENT 40. The autophagy inhibitor of embodiment 26, wherein the aneurysm is an aortic aneurysm.

EMBODIMENT 41. The autophagy inhibitor of embodiment 26, wherein the subject carries a variant affecting the expression of a Thrombospondin Type 1 Domain Containing 1 (THSD1) gene.

EMBODIMENT 42. The autophagy inhibitor of embodiment 41, wherein the variant is in a coding region of the Thrombospondin Type 1 Domain Containing 1 (THSD1) gene.

EMBODIMENT 43. The autophagy inhibitor of embodiment 41, wherein the variant is in a control sequence of a non-coding region of the Thrombospondin Type 1 Domain Containing 1 (THSD1) gene.

EMBODIMENT 44. The autophagy inhibitor of embodiment 41, wherein the variant in the THSD1 gene is a single codon substitution in at least one THSD1 allele.

EMBODIMENT 45. The autophagy inhibitor of embodiment 44, wherein the single codon substitution is L5F, R460W, E466G, G600E, P639L, T653I, or S775P.

EMBODIMENT 46. The autophagy inhibitor of embodiment 26, wherein the therapeutically effective dose of the autophagy inhibitor is administered systemically.

EMBODIMENT 47. The autophagy inhibitor of embodiment 46, wherein systemic administration includes, but is not limited to: (i) intravenous; (ii) intra-arterial; (iii) subcutaneous; or (iv) intraperitoneal.

EMBODIMENT 48. The autophagy inhibitor of embodiment 26, wherein the therapeutically effective dose of the autophagy inhibitor is administered is administered locally.

EMBODIMENT 49. The autophagy inhibitor of embodiment 48, wherein local administration includes, but is not limited to, (i) intracranial; (ii) intra-ocular; (iii) intra-nasal; (iv) intrathecal or (v) intra-vescular.

EMBODIMENT 50. The autophagy inhibitor of embodiment 26, wherein the subject is a human.

EMBODIMENT 51. The use of an autophagy inhibitor of any one of embodiments 26-50 in the manufacture of a medicament for the treatment of an aneurysm.

EMBODIMENT 52. A kit comprising an autophagy inhibitor of any one of embodiments 26-50 and instructions for use thereof.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

The practice of some molecular techniques described herein may employ, unless otherwise indicated, techniques and descriptions of molecular biology (including recombinant techniques), cell biology, biochemistry, and genetic engineering technology, which are within the skill of those who practice in the art. Such techniques and descriptions can be found in standard laboratory manuals such as Westerfield, M. (2000). The zebrafish book. A guide for the laboratory use of zebrafish (*Danio rerio*). 4th ed., Univ. of Oregon Press, Eugene; all of which are herein incorporated in their entirety by reference for all purposes.

Example 1: Molecular Dissection of THSD1 Function in Vascular Endothelial Cells from Global Transcriptomics Genetic factors play a significant role in IA pathogenesis as illustrated by family studies and several IA predisposing syndromes. 7%-20% of all patients have a known family history and a family history is the strongest risk factor for disease. Excluding syndromes that account for less than 1% of all IA cases, candidate IA genes have been primarily identified by genome-wide association studies and more recently, by whole exome sequencing in affected families. Yet, little is known about the genetic causes of IA providing minimum insight for the understanding and development of therapeutic targets that could treat the disease.

Single-family genetic studies are a powerful tool to identify candidate high-risk genetic variants. FIG. 1A illustrates a large family pedigree studied as part of the present disclosure to identify novel candidate genes whose rare variants cause intracranial aneurysm. Specifically, we studied three large IA/SAH families with at least 4 affected individuals where whole exome sequencing has been performed to identify rare variants that segregate with disease. For each family, whole exome sequencing has been performed on at least 15 family members, irrespective of their IA status.

Deleterious Thrombospondin-type 1 domain-containing protein 1 (THSD1) rare variants cause disease in both familial and sporadic cases with supporting evidence from animal models. THSD1 is predominantly expressed in vascular endothelial cells. The work identified deleterious variants in thrombospondin-type 1 domain-containing protein 1 (THSD1) that can cause IA and SAH. Initial characterization of Thsd1 in two vertebrate models including zebrafish and mice lead to the discovery that THSD1 mediated cerebral hemorrhage is located in subarachnoid space in mice. For further description of this work see. Z. Xu, D. Kim, et al., NeuroMolecular Medicine (2019) 21:325-343; T. Santiago-Sim, D. Kim, et al., Stroke. 2016; 47:3005-3013. DOI: 10.1161/STROKEAHA.116.014161); Yan-Ning Rui and D. Kim, et al., Cell Physiol Biochem 2017; 43:2200-2211; each of which incorporated by reference).

However, the mechanism of action utilized by the discovered THSD1 variants to drive disease remained elusive. Further, there was little information describing genes and pathways regulated by THSD1 using global transcriptomics that could be used to inform the mechanism of action of THSD1. Thus, on its own the identification of THSD1 in the context of AI was not sufficient to inform a therapeutic strategy.

The present disclosure contemplated that THSD1 regulated genes may contribute to IA pathogenesis and that modulating their function may be beneficial as an IA treatment or in other diseases with aberrant THSD1 expression. The present disclosure provides results from global transcriptome profiling in human vascular endothelial cells upon THSD1 knockdown that identifies THSD1-regulated specific genes and pathways that are critical for mediating its function, providing potential targets for therapeutic intervention in IA.

The instant disclosure provides RNAseq experiments in two THSD1 knock-down endothelial cell lines. The RNAseq results from both cell lines support the evidence that THSD1 regulates multiple signaling pathways: Integrin, Src, PI3/AKT/mTor, and Rho signaling that are functionally linked to Focal Adhesion Kinase (FAK) signaling. A few of these pathways were selected for further analysis and characterization.

Materials and Methods

Cell Culture

HEK293T cells were maintained in DMEM medium (Corning, 10-013-CV) containing 10% fetal bovine serum (Invitrogen, 10082147), 100 IU penicillin, and 100 µg/ml streptomycin. Transfections of small interfering RNAs and plasmid DNA were performed using lipofectamine 2000 (Life Technologies, 11668027) according to the manufacturer's instructions. Alternatively, for cells such as endothelial cells that are hard to transfect, we will utilize lentiviral system to generate stable cell lines.

Knock-Down Experiments

Knockdown experiments in human vascular endothelial cells were performed using two distinct cell lines [HUVECs and Human brain microvascular endothelial cells (HBMECs)] using four siRNAs (two control siRNAs and two THSD1-specific siRNAs) to minimize erroneous findings due to off-target effects.

Transcriptome Profiling

Bioinformatic analyses of the global transcriptome were performed on rRNA-depleted RNA samples by RNA-Seq. Table 1 illustrates results of the analysis. As shown on Table 1, THSD1 regulates multiple signaling pathways: Integrin, Src, PI3/AKT/mTor, and Rho signaling that are functionally linked to Focal Adhesion Kinase (FAK) signaling) as well as TGFβ signaling.

TABLE 1

Statistically Significant THSD1-Regulated Pathways
(p-value < 0.005; Efron-Tibshirani's GSA test)
Description Integrin Signaling
PI3K/Akt/mTOR Signaling
Src Signaling
Rho Signaling
Tgfβ

We identified a number of genes that are affected by the lack of THSD1 in the knock-down cell lines and are likely regulated by THSD1. A subset of these genes likely contributes to disease pathobiology and may be targets for therapeutic intervention. Table 2. Describes genes differentially expressed in THSD1 knockdowns.

TABLE 2

Genes differentially expressed in THSD1 knockdowns; human brain microvascular endothelial cells and HUVECs, combined

| Description | Genes |
|---|---|
| Differential Expression upon THSD1 Loss Upregulated genes | ALOX5AP, ARL17B, CTSS, GUK1, IFNAR2, LAMC2, NHLRC4, NISCH, OLFML3, PSMD11, PUM2, SLC37A1, SMAP1, SNORA27, TMEM50B, UBAP2, ZNF780A |
| Differential Expression upon THSD1 Loss Downregulated genes | ABCG2, ADAMTS1, AQP1, BCAP31, CDC45, CHCHD7, DMD, ENOX2, FAM219A, FGF2, FGFR1OP2, GOS2, GJA4, IGFBP3, INAFM1, MAP2, MGP, NOL3, NPR1, NVL, PPHLN1, SERPINB2, SETBP1, (THSD1), TMEM107, ZNF185 |

Table 3. lists genes differentially expressed in THSD1 knockdown HUVECs.

TABLE 3

Differentially Expressed Genes in THSD1 Knockdown HUVECs

| Ensembl Gene | Gene Name | logFC | logCPM | LR | PValue | FDR |
|---|---|---|---|---|---|---|
| ENSG00000136114 | THSD1 | −2.07 | 4.85 | 141.12 | 1.52E−32 | 2.15E−28 |
| ENSG00000265107 | GJA5 | −3.81 | 3.42 | 137.13 | 1.13E−31 | 8.01E−28 |
| ENSG00000130066 | SAT1 | −1.74 | 8.37 | 128.15 | 1.04E−29 | 4.92E−26 |
| ENSG00000111341 | MGP | −1.46 | 6.50 | 112.09 | 3.42E−26 | 1.21E−22 |
| ENSG00000187513 | GJA4 | −2.29 | 4.32 | 102.47 | 4.39E−24 | 1.25E−20 |
| ENSG00000284057 | AP001273.2 | 8.67 | −0.99 | 71.34 | 3.00E−17 | 7.11E−14 |
| ENSG00000170323 | FABP4 | −2.09 | 6.36 | 66.29 | 3.90E−16 | 7.91E−13 |
| ENSG00000125266 | EFNB2 | −1.28 | 7.77 | 63.28 | 1.79E−15 | 3.18E−12 |
| ENSG00000113389 | NPR3 | −3.16 | 1.25 | 56.87 | 4.65E−14 | 7.35E−11 |
| ENSG00000134668 | SPOCD1 | 1.16 | 5.45 | 54.03 | 1.97E−13 | 2.80E−10 |
| ENSG00000118777 | ABCG2 | −2.38 | 4.92 | 51.45 | 7.36E−13 | 9.50E−10 |

TABLE 3-continued

Differentially Expressed Genes in THSD1 Knockdown HUVECs

| Ensembl Gene | Gene Name | logFC | logCPM | LR | PValue | FDR |
|---|---|---|---|---|---|---|
| ENSG00000203812 | HIST2H2AA3 | 4.21 | 0.20 | 50.59 | 1.14E−12 | 1.35E−09 |
| ENSG00000272921 | AC005832.4 | −8.85 | −0.72 | 48.91 | 2.69E−12 | 2.93E−09 |
| ENSG00000078018 | MAP2 | −1.06 | 4.84 | 48.51 | 3.29E−12 | 3.34E−09 |
| ENSG00000115884 | SDC1 | −1.53 | 3.23 | 48.33 | 3.61E−12 | 3.42E−09 |
| ENSG00000139278 | GLIPR1 | 1.13 | 6.53 | 47.73 | 4.89E−12 | 4.34E−09 |
| ENSG00000101335 | MYL9 | 1.09 | 4.76 | 47.07 | 6.83E−12 | 5.71E−09 |
| ENSG00000181634 | TNFSF15 | 1.64 | 5.10 | 45.62 | 1.43E−11 | 1.13E−08 |
| ENSG00000122861 | PLAU | 1.03 | 5.58 | 43.85 | 3.55E−11 | 2.65E−08 |
| ENSG00000107551 | RASSF4 | −1.10 | 5.07 | 43.68 | 3.86E−11 | 2.74E−08 |
| ENSG00000274611 | TBC1D3 | −7.97 | −1.52 | 43.13 | 5.12E−11 | 3.46E−08 |
| ENSG00000149591 | TAGLN | 1.81 | 2.54 | 42.71 | 6.35E−11 | 4.10E−08 |
| ENSG00000171435 | KSR2 | 1.18 | 3.90 | 38.39 | 5.80E−10 | 3.58E−07 |
| ENSG00000153165 | RGPD3 | 4.26 | −1.48 | 37.47 | 9.26E−10 | 5.48E−07 |
| ENSG00000251569 | AC093899.2 | 7.32 | −2.20 | 34.85 | 3.55E−09 | 2.02E−06 |
| ENSG00000163083 | INHBB | −2.57 | 2.18 | 34.75 | 3.75E−09 | 2.05E−06 |
| ENSG00000272949 | AC093668.2 | −7.24 | −2.15 | 33.67 | 6.51E−09 | 3.43E−06 |
| ENSG00000152217 | SETBP1 | −1.78 | 3.75 | 33.17 | 8.42E−09 | 4.27E−06 |
| ENSG00000119900 | OGFRL1 | 0.85 | 6.59 | 32.79 | 1.03E−08 | 5.02E−06 |
| ENSG00000082684 | SEMA5B | −4.57 | −1.62 | 32.23 | 1.37E−08 | 6.26E−06 |
| ENSG00000169604 | ANTXR1 | 0.98 | 5.91 | 32.24 | 1.36E−08 | 6.26E−06 |
| ENSG00000137573 | SULF1 | −1.27 | 5.03 | 31.88 | 1.64E−08 | 7.29E−06 |
| ENSG00000115232 | ITGA4 | 1.35 | 3.29 | 30.82 | 2.83E−08 | 1.22E−05 |
| ENSG00000058085 | LAMC2 | 1.06 | 5.71 | 30.05 | 4.21E−08 | 1.76E−05 |
| ENSG00000022567 | SLC45A4 | −1.35 | 3.07 | 29.70 | 5.04E−08 | 1.99E−05 |
| ENSG00000172602 | RND1 | −1.74 | 1.64 | 29.71 | 5.03E−08 | 1.99E−05 |
| ENSG00000103426 | CORO7-PAM16 | 4.38 | −1.48 | 29.02 | 7.16E−08 | 2.75E−05 |
| ENSG00000120217 | CD274 | 1.35 | 4.21 | 28.77 | 8.14E−08 | 3.04E−05 |
| ENSG00000116667 | C1orf21 | −0.99 | 4.42 | 27.88 | 1.29E−07 | 4.70E−05 |
| ENSG00000169129 | AFAP1L2 | −2.16 | 3.16 | 27.67 | 1.44E−07 | 5.10E−05 |
| ENSG00000138646 | HERC5 | −1.85 | 1.47 | 27.51 | 1.56E−07 | 5.29E−05 |
| ENSG00000197646 | PDCD1LG2 | 1.07 | 3.58 | 27.55 | 1.53E−07 | 5.29E−05 |
| ENSG00000064651 | SLC12A2 | 0.73 | 7.05 | 26.91 | 2.13E−07 | 7.03E−05 |
| ENSG00000171388 | APLN | 0.85 | 9.85 | 26.02 | 3.39E−07 | 0.000109 |
| ENSG00000175426 | PCSK1 | 1.51 | 2.68 | 25.80 | 3.79E−07 | 0.00012 |
| ENSG00000057019 | DCBLD2 | 0.91 | 6.78 | 25.67 | 4.05E−07 | 0.000125 |
| ENSG00000008517 | IL32 | 0.69 | 6.11 | 25.52 | 4.37E−07 | 0.000132 |
| ENSG00000138685 | FGF2 | −1.20 | 5.72 | 25.21 | 5.15E−07 | 0.000152 |
| ENSG00000065308 | TRAM2 | 0.67 | 8.10 | 25.04 | 5.60E−07 | 0.000162 |
| ENSG00000137507 | LRRC32 | −0.87 | 7.22 | 24.74 | 6.57E−07 | 0.000187 |
| ENSG00000129116 | PALLD | 0.69 | 6.27 | 24.56 | 7.22E−07 | 0.000201 |
| ENSG00000129521 | EGLN3 | −1.85 | 0.09 | 24.44 | 7.66E−07 | 0.000209 |
| ENSG00000125954 | CHURC1-FNTB | −6.59 | −2.67 | 24.25 | 8.46E−07 | 0.000227 |
| ENSG00000152402 | GUCY1A2 | 1.90 | 1.31 | 24.20 | 8.68E−07 | 0.000228 |
| ENSG00000169429 | CXCL8 | 1.22 | 4.62 | 23.66 | 1.15E−06 | 0.000297 |
| ENSG00000164683 | HEY1 | −1.25 | 3.49 | 23.30 | 1.38E−06 | 0.000345 |
| ENSG00000176907 | TCIM | 0.95 | 3.77 | 23.31 | 1.38E−06 | 0.000345 |
| ENSG00000082126 | MPP4 | 0.76 | 4.76 | 23.08 | 1.56E−06 | 0.000379 |
| ENSG00000163637 | PRICKLE2 | −0.99 | 3.76 | 23.06 | 1.57E−06 | 0.000379 |
| ENSG00000148143 | ZNF462 | 0.72 | 4.95 | 22.92 | 1.69E−06 | 0.0004 |
| ENSG00000139289 | PHLDA1 | 0.63 | 7.00 | 22.22 | 2.43E−06 | 0.000566 |
| ENSG00000028137 | TNFRSF1B | −0.99 | 6.14 | 22.02 | 2.69E−06 | 0.000617 |
| ENSG00000139629 | GALNT6 | 0.66 | 5.98 | 21.94 | 2.82E−06 | 0.000635 |
| ENSG00000117586 | TNFSF4 | 0.66 | 7.43 | 21.80 | 3.03E−06 | 0.000672 |
| ENSG00000256514 | AP003419.1 | 1.68 | 0.91 | 21.47 | 3.60E−06 | 0.000787 |
| ENSG00000240583 | AQP1 | −1.84 | 3.43 | 21.27 | 3.99E−06 | 0.000858 |
| ENSG00000115252 | PDE1A | −2.04 | 0.57 | 21.17 | 4.20E−06 | 0.00089 |
| ENSG00000178695 | KCTD12 | −0.71 | 8.94 | 20.99 | 4.62E−06 | 0.000965 |
| ENSG00000173535 | TNFRSF10C | −0.65 | 6.69 | 20.89 | 4.87E−06 | 0.001002 |
| ENSG00000156298 | TSPAN7 | −1.50 | 3.22 | 20.81 | 5.08E−06 | 0.001031 |
| ENSG00000037280 | FLT4 | −0.95 | 6.22 | 20.66 | 5.48E−06 | 0.001066 |
| ENSG00000118515 | SGK1 | 1.02 | 6.19 | 20.70 | 5.37E−06 | 0.001066 |
| ENSG00000171105 | INSR | −0.82 | 5.20 | 20.67 | 5.47E−06 | 0.001066 |
| ENSG00000128917 | DLL4 | −1.06 | 6.99 | 20.55 | 5.81E−06 | 0.001116 |
| ENSG00000164284 | GRPEL2 | 0.71 | 5.83 | 20.28 | 6.70E−06 | 0.001268 |
| ENSG00000130449 | ZSWIM6 | 0.84 | 6.22 | 20.20 | 6.96E−06 | 0.0013 |
| ENSG00000165029 | ABCA1 | −1.20 | 4.86 | 20.18 | 7.06E−06 | 0.001303 |
| ENSG00000143127 | ITGA10 | −0.95 | 4.84 | 20.08 | 7.43E−06 | 0.001336 |
| ENSG00000187720 | THSD4 | 0.77 | 5.68 | 20.08 | 7.43E−06 | 0.001336 |
| ENSG00000073008 | PVR | 0.69 | 7.34 | 19.90 | 8.14E−06 | 0.001422 |
| ENSG00000107731 | UNC5B | −1.58 | 3.90 | 19.93 | 8.03E−06 | 0.001422 |
| ENSG00000122786 | CALD1 | 0.71 | 9.31 | 19.89 | 8.21E−06 | 0.001422 |
| ENSG00000110092 | CCND1 | 0.77 | 8.26 | 19.76 | 8.76E−06 | 0.0015 |
| ENSG00000154734 | ADAMTS1 | −1.32 | 3.65 | 19.66 | 9.23E−06 | 0.001561 |
| ENSG00000142178 | SIK1 | 1.16 | 2.11 | 19.62 | 9.46E−06 | 0.001581 |
| ENSG00000168843 | FSTL5 | 1.55 | 0.35 | 19.53 | 9.92E−06 | 0.001638 |
| ENSG00000121858 | TNFSF10 | −0.94 | 4.92 | 19.41 | 1.05E−05 | 0.001722 |

TABLE 3-continued

Differentially Expressed Genes in THSD1 Knockdown HUVECs

| Ensembl Gene | Gene Name | logFC | logCPM | LR | PValue | FDR |
|---|---|---|---|---|---|---|
| ENSG00000169213 | RAB3B | 0.71 | 5.47 | 19.35 | 1.09E-05 | 0.001754 |
| ENSG00000166670 | MMP10 | 1.61 | 6.00 | 19.29 | 1.12E-05 | 0.00179 |
| ENSG00000138347 | MYPN | 2.35 | -1.12 | 19.03 | 1.29E-05 | 0.002029 |
| ENSG00000145247 | OCIAD2 | 0.76 | 5.62 | 18.90 | 1.38E-05 | 0.002126 |
| ENSG00000160801 | PTH1R | -2.70 | -1.67 | 18.89 | 1.38E-05 | 0.002126 |
| ENSG00000184113 | CLDN5 | -0.91 | 7.73 | 18.88 | 1.39E-05 | 0.002126 |
| ENSG00000152518 | ZFP36L2 | -0.62 | 6.87 | 18.76 | 1.48E-05 | 0.002235 |
| ENSG00000171617 | ENC1 | 0.87 | 6.92 | 18.56 | 1.64E-05 | 0.002457 |
| ENSG00000166833 | NAV2 | 0.61 | 5.37 | 18.42 | 1.77E-05 | 0.00262 |
| ENSG00000177076 | ACER2 | -1.05 | 3.11 | 18.28 | 1.91E-05 | 0.002793 |
| ENSG00000154928 | EPHB1 | 1.07 | 2.28 | 18.16 | 2.03E-05 | 0.002915 |
| ENSG00000162407 | PLPP3 | -0.99 | 5.19 | 18.16 | 2.03E-05 | 0.002915 |
| ENSG00000099204 | ABLIM1 | -0.73 | 8.31 | 18.11 | 2.09E-05 | 0.002957 |
| ENSG00000177606 | JUN | 0.68 | 7.59 | 18.09 | 2.10E-05 | 0.002957 |
| ENSG00000170006 | TMEM154 | 0.74 | 5.48 | 18.03 | 2.17E-05 | 0.003026 |
| ENSG00000118762 | PKD2 | -0.61 | 5.46 | 17.91 | 2.32E-05 | 0.003197 |
| ENSG00000108387 | 'SEPT4 | -1.64 | -0.22 | 17.45 | 2.96E-05 | 0.004038 |
| ENSG00000170891 | CYTL1 | 0.91 | 3.83 | 17.25 | 3.28E-05 | 0.004439 |
| ENSG00000175040 | CHST2 | 0.88 | 4.58 | 17.17 | 3.42E-05 | 0.004583 |
| ENSG00000167037 | SGSM1 | -1.41 | 1.33 | 17.15 | 3.45E-05 | 0.004587 |
| ENSG00000185070 | FLRT2 | 0.70 | 7.60 | 17.09 | 3.57E-05 | 0.004694 |
| ENSG00000180304 | OAZ2 | -0.56 | 6.82 | 16.78 | 4.20E-05 | 0.005473 |
| ENSG00000257093 | KIAA1147 | -0.59 | 7.24 | 16.71 | 4.36E-05 | 0.005628 |
| ENSG00000184897 | H1FX | -0.58 | 6.28 | 16.64 | 4.53E-05 | 0.005794 |
| ENSG00000075426 | FOSL2 | 0.57 | 6.66 | 16.52 | 4.80E-05 | 0.006094 |
| ENSG00000105825 | TFPI2 | 0.57 | 7.14 | 16.40 | 5.13E-05 | 0.006449 |
| ENSG00000135318 | NT5E | 0.61 | 7.62 | 16.38 | 5.18E-05 | 0.00645 |
| ENSG00000127533 | F2RL3 | 1.23 | 1.06 | 16.34 | 5.30E-05 | 0.006492 |
| ENSG00000205683 | DPF3 | 1.21 | 2.98 | 16.34 | 5.30E-05 | 0.006492 |
| ENSG00000105499 | PLA2G4C | 0.76 | 3.68 | 16.29 | 5.44E-05 | 0.006599 |
| ENSG00000167984 | NLRC3 | 0.99 | 2.82 | 16.02 | 6.26E-05 | 0.007507 |
| ENSG00000168685 | IL7R | 1.30 | 1.79 | 16.00 | 6.32E-05 | 0.007507 |
| ENSG00000172985 | SH3RF3 | 0.64 | 5.05 | 16.00 | 6.34E-05 | 0.007507 |
| ENSG00000108551 | RASD1 | 1.21 | 2.55 | 15.95 | 6.49E-05 | 0.00762 |
| ENSG00000081087 | OSTM1 | 0.67 | 5.66 | 15.81 | 6.99E-05 | 0.008139 |
| ENSG00000128849 | CGNL1 | -0.78 | 6.46 | 15.61 | 7.78E-05 | 0.008985 |
| ENSG00000133816 | MICAL2 | 0.69 | 7.58 | 15.59 | 7.87E-05 | 0.009013 |
| ENSG00000132965 | ALOX5AP | 2.25 | -1.61 | 15.55 | 8.04E-05 | 0.009132 |
| ENSG00000084734 | GCKR | -2.84 | -1.71 | 15.38 | 8.89E-05 | 0.009794 |
| ENSG00000108854 | SMURF2 | 0.53 | 7.94 | 15.38 | 8.81E-05 | 0.009794 |
| ENSG00000111859 | NEDD9 | 0.52 | 6.27 | 15.36 | 8.89E-05 | 0.009794 |
| ENSG00000154678 | PDE1C | 0.89 | 3.99 | 15.37 | 8.84E-05 | 0.009794 |
| ENSG00000033867 | SLC4A7 | 0.58 | 7.03 | 15.33 | 9.05E-05 | 0.009889 |
| ENSG00000152207 | CYSLTR2 | -2.45 | -0.56 | 15.25 | 9.42E-05 | 0.010156 |
| ENSG00000188452 | CERKL | 1.26 | 0.91 | 15.25 | 9.44E-05 | 0.010156 |
| ENSG00000105357 | MYH14 | 1.43 | 0.19 | 15.20 | 9.66E-05 | 0.010323 |
| ENSG00000185432 | METTL7A | -1.01 | 3.66 | 15.17 | 9.83E-05 | 0.010418 |
| ENSG00000004799 | PDK4 | -1.18 | 2.61 | 15.12 | 0.000101 | 0.010639 |
| ENSG00000122694 | GLIPR2 | 0.65 | 4.88 | 15.10 | 0.000102 | 0.010655 |
| ENSG00000213402 | PTPRCAP | -3.20 | -2.40 | 15.08 | 0.000103 | 0.010665 |
| ENSG00000115902 | SLC1A4 | -0.69 | 4.85 | 14.96 | 0.00011 | 0.011119 |
| ENSG00000169248 | CXCL11 | 1.35 | 0.90 | 14.97 | 0.000109 | 0.011119 |
| ENSG00000189367 | KIAA0408 | 1.83 | -0.79 | 14.96 | 0.00011 | 0.011119 |
| ENSG00000102755 | FLT1 | -0.77 | 8.53 | 14.90 | 0.000114 | 0.011449 |
| ENSG00000135905 | DOCK10 | 0.62 | 5.30 | 14.86 | 0.000116 | 0.01158 |
| ENSG00000079102 | RUNX1T1 | -0.82 | 4.50 | 14.83 | 0.000118 | 0.011588 |
| ENSG00000153208 | MERTK | 0.58 | 5.53 | 14.83 | 0.000118 | 0.011588 |
| ENSG00000198435 | NRARP | -0.63 | 5.05 | 14.82 | 0.000118 | 0.011588 |
| ENSG00000141682 | PMAIP1 | 1.02 | 4.25 | 14.80 | 0.00012 | 0.01165 |
| ENSG00000011347 | SYT7 | -1.86 | -0.09 | 14.71 | 0.000126 | 0.012144 |
| ENSG00000135842 | FAM129A | -1.24 | 1.66 | 14.52 | 0.000139 | 0.013339 |
| ENSG00000020577 | SAMD4A | 0.62 | 5.94 | 14.47 | 0.000143 | 0.013504 |
| ENSG00000143153 | ATP1B1 | 0.74 | 5.54 | 14.47 | 0.000142 | 0.013504 |
| ENSG00000177666 | PNPLA2 | -0.55 | 6.36 | 14.43 | 0.000145 | 0.013671 |
| ENSG00000085276 | MECOM | -0.53 | 7.33 | 14.39 | 0.000148 | 0.013802 |
| ENSG00000111145 | ELK3 | -0.64 | 8.64 | 14.39 | 0.000149 | 0.013802 |
| ENSG00000140675 | SLC5A2 | -5.88 | -3.18 | 14.34 | 0.000152 | 0.014056 |
| ENSG00000005108 | THSD7A | -0.61 | 5.99 | 14.27 | 0.000159 | 0.014543 |
| ENSG00000157613 | CREB3L1 | 1.04 | 1.76 | 14.23 | 0.000162 | 0.014743 |
| ENSG00000163584 | RPL22L1 | -0.61 | 5.30 | 14.18 | 0.000166 | 0.015011 |
| ENSG00000169418 | NPR1 | -1.45 | 3.01 | 14.12 | 0.000171 | 0.015403 |
| ENSG00000131016 | AKAP12 | 0.59 | 10.29 | 14.07 | 0.000176 | 0.015751 |
| ENSG00000141298 | SSH2 | 0.55 | 6.75 | 13.98 | 0.000184 | 0.016299 |
| ENSG00000163131 | CTSS | 0.96 | 2.75 | 13.98 | 0.000185 | 0.016299 |
| ENSG00000026508 | CD44 | 0.69 | 5.54 | 13.94 | 0.000189 | 0.016335 |
| ENSG00000136404 | TM6SF1 | 0.69 | 4.25 | 13.92 | 0.00019 | 0.016335 |

TABLE 3-continued

Differentially Expressed Genes in THSD1 Knockdown HUVECs

| Ensembl Gene | Gene Name | logFC | logCPM | LR | PValue | FDR |
| --- | --- | --- | --- | --- | --- | --- |
| ENSG00000144583 | 'MARCH4 | 0.82 | 5.53 | 13.95 | 0.000188 | 0.016335 |
| ENSG00000175899 | A2M | −1.56 | 2.41 | 13.92 | 0.000191 | 0.016335 |
| ENSG00000176749 | CDK5R1 | 1.01 | 2.89 | 13.94 | 0.000189 | 0.016335 |
| ENSG00000258984 | UBE2F-SCLY | 3.28 | −1.94 | 13.88 | 0.000194 | 0.016538 |
| ENSG00000136960 | ENPP2 | −1.14 | 1.35 | 13.86 | 0.000197 | 0.016639 |
| ENSG00000140416 | TPM1 | 0.61 | 8.65 | 13.81 | 0.000202 | 0.016977 |
| ENSG00000112541 | PDE10A | −0.92 | 3.09 | 13.76 | 0.000208 | 0.017288 |
| ENSG00000198286 | CARD11 | 0.59 | 5.90 | 13.76 | 0.000208 | 0.017288 |
| ENSG00000108825 | PTGES3L-AARSD1 | 1.90 | −0.91 | 13.67 | 0.000218 | 0.017886 |
| ENSG00000185650 | ZFP36L1 | 0.51 | 6.82 | 13.66 | 0.000219 | 0.017886 |
| ENSG00000188290 | HES4 | −1.30 | 2.20 | 13.66 | 0.000219 | 0.017886 |
| ENSG00000114631 | PODXL2 | 0.66 | 4.05 | 13.62 | 0.000224 | 0.018189 |
| ENSG00000106852 | LHX6 | 0.94 | 4.20 | 13.59 | 0.000227 | 0.018332 |
| ENSG00000171115 | GIMAP8 | −0.63 | 7.66 | 13.56 | 0.000231 | 0.018514 |
| ENSG00000189120 | SP6 | 1.04 | 1.77 | 13.54 | 0.000234 | 0.018568 |
| ENSG00000265972 | TXNIP | −1.35 | 3.74 | 13.54 | 0.000234 | 0.018568 |
| ENSG00000154639 | CXADR | 0.57 | 4.98 | 13.51 | 0.000237 | 0.018606 |
| ENSG00000169242 | EFNA1 | −0.75 | 6.23 | 13.52 | 0.000237 | 0.018606 |
| ENSG00000204304 | PBX2 | −0.72 | 5.80 | 13.49 | 0.00024 | 0.018755 |
| ENSG00000157557 | ETS2 | 0.56 | 6.59 | 13.45 | 0.000244 | 0.018975 |
| ENSG00000105855 | ITGB8 | 1.01 | 3.67 | 13.44 | 0.000246 | 0.018999 |
| ENSG00000144802 | NFKBIZ | 0.88 | 4.33 | 13.37 | 0.000255 | 0.019615 |
| ENSG00000204262 | COL5A2 | 0.51 | 8.22 | 13.33 | 0.000262 | 0.019978 |
| ENSG00000163092 | XIRP2 | 2.56 | −0.54 | 13.31 | 0.000264 | 0.020085 |
| ENSG00000049540 | ELN | −2.37 | −1.72 | 13.23 | 0.000275 | 0.020704 |
| ENSG00000166341 | DCHS1 | 0.50 | 7.06 | 13.24 | 0.000274 | 0.020704 |
| ENSG00000115414 | FN1 | 0.69 | 12.30 | 13.17 | 0.000284 | 0.021259 |
| ENSG00000094880 | CDC23 | −0.63 | 5.49 | 13.10 | 0.000295 | 0.021903 |
| ENSG00000164647 | STEAP1 | −0.67 | 4.33 | 13.10 | 0.000296 | 0.021903 |
| ENSG00000119681 | LTBP2 | 0.48 | 9.54 | 13.03 | 0.000306 | 0.022511 |
| ENSG00000107562 | CXCL12 | 2.40 | −1.46 | 12.98 | 0.000314 | 0.022927 |
| ENSG00000138448 | ITGAV | 0.55 | 8.76 | 12.96 | 0.000318 | 0.022927 |
| ENSG00000160223 | ICOSLG | −0.72 | 3.61 | 12.95 | 0.00032 | 0.022927 |
| ENSG00000163644 | PPM1K | −0.64 | 3.93 | 12.96 | 0.000318 | 0.022927 |
| ENSG00000186575 | NF2 | 0.58 | 6.53 | 12.95 | 0.000319 | 0.022927 |
| ENSG00000109906 | ZBTB16 | −1.08 | 1.12 | 12.94 | 0.000322 | 0.022986 |
| ENSG00000144476 | ACKR3 | −0.77 | 4.06 | 12.89 | 0.00033 | 0.023468 |
| ENSG00000136011 | STAB2 | −3.99 | −2.80 | 12.86 | 0.000335 | 0.023698 |
| ENSG00000074181 | NOTCH3 | −1.01 | 1.47 | 12.84 | 0.000338 | 0.023798 |
| ENSG00000168916 | ZNF608 | −0.63 | 5.15 | 12.72 | 0.000362 | 0.025298 |
| ENSG00000076351 | SLC46A1 | 0.82 | 2.77 | 12.71 | 0.000364 | 0.025315 |
| ENSG00000151474 | FRMD4A | 0.53 | 7.31 | 12.66 | 0.000374 | 0.025951 |
| ENSG00000139508 | SLC46A3 | −1.45 | 4.08 | 12.58 | 0.00039 | 0.026876 |
| ENSG00000131386 | GALNT15 | −1.70 | 0.16 | 12.53 | 0.000401 | 0.027499 |
| ENSG00000101017 | CD40 | −0.65 | 4.42 | 12.49 | 0.000409 | 0.027854 |
| ENSG00000270316 | BORCS7-ASMT | −6.14 | −3.00 | 12.49 | 0.00041 | 0.027854 |
| ENSG00000141668 | CBLN2 | 2.75 | 0.19 | 12.48 | 0.000412 | 0.027879 |
| ENSG00000146072 | TNFRSF21 | 0.47 | 6.64 | 12.44 | 0.000419 | 0.028234 |
| ENSG00000183287 | CCBE1 | 1.06 | 1.39 | 12.39 | 0.000432 | 0.028931 |
| ENSG00000029534 | ANK1 | −1.37 | 0.01 | 12.37 | 0.000436 | 0.029068 |
| ENSG00000124593 | AL365205.1 | −0.90 | 3.18 | 12.35 | 0.00044 | 0.029134 |
| ENSG00000281028 | AC104662.2 | −6.09 | −3.04 | 12.35 | 0.000441 | 0.029134 |
| ENSG00000187942 | LDLRAD2 | −0.76 | 3.41 | 12.33 | 0.000446 | 0.029332 |
| ENSG00000071246 | VASH1 | −0.66 | 7.76 | 12.30 | 0.000453 | 0.029655 |
| ENSG00000269307 | AC010463.1 | −6.06 | −3.06 | 12.27 | 0.000461 | 0.030027 |
| ENSG00000050405 | LIMA1 | 0.47 | 7.26 | 12.26 | 0.000463 | 0.030037 |
| ENSG00000259171 | AL163636.2 | −1.37 | 1.58 | 12.25 | 0.000465 | 0.030049 |
| ENSG00000048740 | CELF2 | 0.49 | 6.23 | 12.18 | 0.000483 | 0.030936 |
| ENSG00000116774 | OLFML3 | 0.99 | 1.45 | 12.18 | 0.000482 | 0.030936 |
| ENSG00000182240 | BACE2 | −0.56 | 7.52 | 12.17 | 0.000486 | 0.030971 |
| ENSG00000204767 | FAM196B | 0.77 | 3.39 | 12.15 | 0.00049 | 0.031102 |
| ENSG00000211448 | DIO2 | 2.26 | −1.84 | 12.14 | 0.000494 | 0.031198 |
| ENSG00000151468 | CCDC3 | −1.17 | 0.72 | 12.11 | 0.000501 | 0.031481 |
| ENSG00000196498 | NCOR2 | 0.52 | 7.49 | 12.09 | 0.000506 | 0.031651 |
| ENSG00000049130 | KITLG | 0.70 | 5.16 | 12.07 | 0.000512 | 0.031901 |
| ENSG00000137033 | IL33 | −1.94 | 4.40 | 12.06 | 0.000516 | 0.031997 |
| ENSG00000130635 | COL5A1 | 0.52 | 8.58 | 12.03 | 0.000524 | 0.032215 |
| ENSG00000133056 | PIK3C2B | −0.67 | 5.90 | 12.03 | 0.000522 | 0.032215 |
| ENSG00000116741 | RGS2 | 0.79 | 3.02 | 12.02 | 0.000528 | 0.0323 |
| ENSG00000129757 | CDKN1C | −0.95 | 2.05 | 11.98 | 0.000536 | 0.032564 |
| ENSG00000179195 | ZNF664 | −0.66 | 6.99 | 11.99 | 0.000535 | 0.032564 |
| ENSG00000185924 | RTN4RL1 | −2.85 | −2.54 | 11.97 | 0.000542 | 0.032704 |
| ENSG00000189060 | H1F0 | −0.50 | 6.44 | 11.96 | 0.000543 | 0.032704 |
| ENSG00000255767 | AC108488.2 | 5.64 | −3.35 | 11.95 | 0.000548 | 0.032834 |
| ENSG00000108691 | CCL2 | 0.56 | 5.05 | 11.89 | 0.000566 | 0.033765 |

TABLE 3-continued

Differentially Expressed Genes in THSD1 Knockdown HUVECs

| Ensembl Gene | Gene Name | logFC | logCPM | LR | PValue | FDR |
|---|---|---|---|---|---|---|
| ENSG00000106069 | CHN2 | 0.83 | 2.52 | 11.87 | 0.000571 | 0.033914 |
| ENSG00000132702 | HAPLN2 | 1.07 | 3.28 | 11.85 | 0.000575 | 0.033914 |
| ENSG00000183691 | NOG | 1.96 | 0.87 | 11.85 | 0.000575 | 0.033914 |
| ENSG00000105738 | SIPA1L3 | 0.53 | 5.37 | 11.84 | 0.000578 | 0.033924 |
| ENSG00000154096 | THY1 | −1.73 | 0.37 | 11.84 | 0.00058 | 0.033924 |
| ENSG00000140937 | CDH11 | 0.58 | 5.50 | 11.80 | 0.000592 | 0.034495 |
| ENSG00000127241 | MASP1 | −1.60 | −0.50 | 11.77 | 0.000601 | 0.034815 |
| ENSG00000164574 | GALNT10 | 0.47 | 7.18 | 11.77 | 0.000603 | 0.034815 |
| ENSG00000259112 | NDUFC2-KCTD14 | 5.59 | −3.38 | 11.75 | 0.000609 | 0.035044 |
| ENSG00000109046 | WSB1 | −0.57 | 8.59 | 11.72 | 0.000619 | 0.035055 |
| ENSG00000130054 | FAM155B | 1.73 | −1.28 | 11.72 | 0.000619 | 0.035055 |
| ENSG00000133401 | PDZD2 | −0.68 | 3.72 | 11.72 | 0.000618 | 0.035055 |
| ENSG00000284041 | AC073111.3 | −5.87 | −3.18 | 11.72 | 0.000619 | 0.035055 |
| ENSG00000115008 | IL1A | 1.56 | 1.13 | 11.67 | 0.000634 | 0.035722 |
| ENSG00000185737 | NRG3 | −0.86 | 2.50 | 11.66 | 0.000638 | 0.035834 |
| ENSG00000196923 | PDLIM7 | 0.57 | 7.15 | 11.64 | 0.000644 | 0.036026 |
| ENSG00000187583 | PLEKHN1 | 1.60 | −1.07 | 11.62 | 0.000652 | 0.036337 |
| ENSG00000135324 | MRAP2 | −0.97 | 3.21 | 11.57 | 0.000672 | 0.037286 |
| ENSG00000158186 | MRAS | 0.56 | 4.27 | 11.55 | 0.000678 | 0.037503 |
| ENSG00000092969 | TGFB2 | 1.40 | 3.41 | 11.54 | 0.000682 | 0.037523 |
| ENSG00000158373 | HIST1H2BD | 1.95 | 0.56 | 11.53 | 0.000684 | 0.037523 |
| ENSG00000118946 | PCDH17 | 1.00 | 3.06 | 11.49 | 0.0007 | 0.038238 |
| ENSG00000067798 | NAV3 | 0.64 | 5.24 | 11.48 | 0.000705 | 0.038357 |
| ENSG00000143344 | RGL1 | 0.81 | 6.48 | 11.46 | 0.00071 | 0.03848 |
| ENSG00000188042 | ARL4C | 0.65 | 3.97 | 11.43 | 0.000723 | 0.039053 |
| ENSG00000162772 | ATF3 | 0.98 | 1.96 | 11.41 | 0.000731 | 0.039331 |
| ENSG00000164104 | HMGB2 | −0.50 | 7.51 | 11.38 | 0.000742 | 0.039771 |
| ENSG00000138411 | HECW2 | 0.47 | 7.31 | 11.36 | 0.000749 | 0.03998 |
| ENSG00000142627 | EPHA2 | 0.49 | 7.57 | 11.33 | 0.000763 | 0.040464 |
| NSG00000258947 | TUBB3 | 0.62 | 7.55 | 11.33 | 0.000761 | 0.040464 |
| ENSG00000183775 | KCTD16 | 1.30 | −0.12 | 11.30 | 0.000773 | 0.040837 |
| ENSG00000114948 | ADAM23 | 0.55 | 5.15 | 11.26 | 0.000793 | 0.041703 |
| ENSG00000114315 | HES1 | −0.49 | 5.56 | 11.22 | 0.000811 | 0.042315 |
| ENSG00000138772 | ANXA3 | 0.65 | 5.85 | 11.22 | 0.000808 | 0.042315 |
| ENSG00000270276 | HIST2H4B | −1.49 | −0.13 | 11.21 | 0.000813 | 0.042315 |
| ENSG00000213694 | S1PR3 | 0.71 | 4.78 | 11.16 | 0.000835 | 0.043284 |
| ENSG00000150687 | PRSS23 | 0.44 | 9.70 | 11.15 | 0.000841 | 0.043462 |
| ENSG00000095303 | PTGS1 | 0.62 | 4.28 | 11.12 | 0.000852 | 0.043854 |
| ENSG00000146674 | IGFBP3 | −0.93 | 1.59 | 11.11 | 0.00086 | 0.04411 |
| ENSG00000109436 | TBC1D9 | 0.45 | 6.66 | 11.09 | 0.000868 | 0.044376 |
| ENSG00000274933 | TBC1D3I | 3.01 | −2.32 | 11.07 | 0.000879 | 0.044738 |
| ENSG00000116678 | LEPR | −0.62 | 4.60 | 11.04 | 0.000893 | 0.044947 |
| ENSG00000156642 | NPTN | −0.65 | 6.37 | 11.04 | 0.000892 | 0.044947 |
| ENSG00000198720 | ANKRD13B | 0.53 | 4.45 | 11.03 | 0.000895 | 0.044947 |
| ENSG00000228144 | AC078927.1 | 5.57 | −3.50 | 11.04 | 0.000891 | 0.044947 |
| ENSG00000256966 | AL513165.2 | 2.50 | −2.24 | 11.01 | 0.000907 | 0.045379 |
| ENSG00000156920 | ADGRG4 | 3.17 | −2.89 | 10.97 | 0.000926 | 0.046138 |
| ENSG00000171877 | FRMD5 | 0.66 | 4.15 | 10.92 | 0.00095 | 0.047183 |
| ENSG00000164946 | FREM1 | 1.21 | 0.17 | 10.87 | 0.000975 | 0.048254 |
| ENSG00000159640 | ACE | −0.99 | 5.64 | 10.86 | 0.000982 | 0.048417 |
| ENSG00000176771 | NCKAP5 | 1.30 | 0.36 | 10.84 | 0.000993 | 0.048822 |
| ENSG00000198513 | ATL1 | 1.00 | 3.22 | 10.83 | 0.000999 | 0.048942 |
| ENSG00000100234 | TIMP3 | −0.98 | 3.13 | 10.82 | 0.001006 | 0.049108 |

TABLE 4 lists genes differentially expressed in THSD1 knockdown HUVECs
Table 4. Differentially Expressed Genes in THSD1 Knockdown HBMECS

| Ensembl Gene | Gene Symbol | logFC | logCPM | LR | PValue | FDR |
|---|---|---|---|---|---|---|
| ENSG00000117152 | RGS4 | −1.59 | 6.07 | 88.46 | 5.18E−21 | 7.37E−17 |
| ENSG00000272949 | AC093668.2 | 8.74 | −0.80 | 64.63 | 9.02E−16 | 6.40E−12 |
| ENSG00000283088 | AC010487.3 | −8.71 | −0.85 | 60.76 | 6.45E−15 | 3.05E−11 |
| ENSG00000136114 | THSD1 | −1.51 | 4.73 | 58.41 | 2.13E−14 | 7.56E−11 |
| ENSG00000146674 | IGFBP3 | −2.59 | 2.50 | 54.84 | 1.31E−13 | 3.72E−10 |
| ENSG00000284057 | AP001273.2 | 8.19 | −1.30 | 52.15 | 5.15E−13 | 1.22E−09 |
| ENSG00000133101 | CCNA1 | −1.31 | 4.76 | 45.04 | 1.93E−11 | 3.92E−08 |
| ENSG00000078018 | MAP2 | −1.31 | 4.98 | 43.56 | 4.11E−11 | 7.29E−08 |
| ENSG00000240583 | AQP1 | −2.37 | 3.93 | 41.78 | 1.02E−10 | 1.61E−07 |
| ENSG00000008517 | IL32 | 1.06 | 6.45 | 39.73 | 2.92E−10 | 4.15E−07 |
| ENSG00000154734 | ADAMTS1 | −1.55 | 3.82 | 38.76 | 4.78E−10 | 6.18E−07 |

TABLE 4-continued lists genes differentially expressed in THSD1 knockdown HUVECs
Table 4. Differentially Expressed Genes in THSD1 Knockdown HBMECS

| Ensembl Gene | Gene Symbol | logFC | logCPM | LR | PValue | FDR |
|---|---|---|---|---|---|---|
| ENSG00000068489 | PRR11 | −1.00 | 6.19 | 37.14 | 1.10E−09 | 1.30E−06 |
| ENSG00000118777 | ABCG2 | −1.75 | 3.44 | 36.14 | 1.84E−09 | 1.87E−06 |
| ENSG00000168542 | COL3A1 | 2.68 | 1.64 | 36.27 | 1.72E−09 | 1.87E−06 |
| ENSG00000138180 | CEP55 | −0.99 | 6.19 | 35.71 | 2.30E−09 | 2.17E−06 |
| ENSG00000272414 | FAM47E-STBD1 | 4.42 | −1.05 | 35.52 | 2.52E−09 | 2.24E−06 |
| ENSG00000264187 | AC055811.2 | 7.52 | −1.89 | 35.39 | 2.70E−09 | 2.26E−06 |
| ENSG00000072571 | HMMR | −1.09 | 5.70 | 34.95 | 3.39E−09 | 2.67E−06 |
| ENSG00000112984 | KIF20A | −1.03 | 6.21 | 34.59 | 4.07E−09 | 3.05E−06 |
| ENSG00000126787 | DLGAP5 | −0.96 | 6.86 | 34.15 | 5.09E−09 | 3.62E−06 |
| ENSG00000081087 | OSTM1 | 1.10 | 5.56 | 33.06 | 8.93E−09 | 6.04E−06 |
| ENSG00000117399 | CDC20 | −1.02 | 6.40 | 32.40 | 1.25E−08 | 8.08E−06 |
| ENSG00000100292 | HMOX1 | 0.94 | 6.83 | 31.53 | 1.96E−08 | 1.21E−05 |
| ENSG00000134057 | CCNB1 | −0.94 | 6.95 | 31.40 | 2.10E−08 | 1.24E−05 |
| ENSG00000143228 | NUF2 | −1.06 | 5.01 | 30.90 | 2.71E−08 | 1.48E−05 |
| ENSG00000166851 | PLK1 | −1.03 | 6.17 | 30.91 | 2.70E−08 | 1.48E−05 |
| ENSG00000108691 | CCL2 | 1.38 | 5.33 | 29.45 | 5.74E−08 | 2.86E−05 |
| ENSG00000132470 | ITGB4 | −1.94 | 3.69 | 29.41 | 5.84E−08 | 2.86E−05 |
| ENSG00000164104 | HMGB2 | −0.86 | 7.35 | 29.54 | 5.47E−08 | 2.86E−05 |
| ENSG00000163661 | PTX3 | −1.01 | 7.71 | 29.11 | 6.85E−08 | 3.24E−05 |
| ENSG00000145386 | CCNA2 | −1.01 | 6.45 | 29.03 | 7.12E−08 | 3.26E−05 |
| ENSG00000142945 | KIF2C | −0.95 | 5.36 | 28.79 | 8.07E−08 | 3.58E−05 |
| ENSG00000146678 | IGFBP1 | −2.51 | 0.45 | 28.44 | 9.65E−08 | 4.15E−05 |
| ENSG00000137812 | KNL1 | −1.09 | 5.81 | 28.26 | 1.06E−07 | 4.44E−05 |
| ENSG00000138182 | KIF20B | −1.01 | 5.81 | 28.10 | 1.15E−07 | 4.67E−05 |
| ENSG00000080986 | NDC80 | −1.05 | 5.15 | 27.56 | 1.52E−07 | 5.90E−05 |
| ENSG00000136928 | GABBR2 | −0.95 | 6.03 | 27.44 | 1.62E−07 | 5.90E−05 |
| ENSG00000137804 | NUSAP1 | −0.95 | 6.08 | 27.46 | 1.60E−07 | 5.90E−05 |
| ENSG00000273294 | C1QTNF3-AMACR | 7.05 | −2.28 | 27.45 | 1.62E−07 | 5.90E−05 |
| ENSG00000131747 | TOP2A | −0.97 | 8.09 | 26.97 | 2.07E−07 | 7.35E−05 |
| ENSG00000087586 | AURKA | −0.86 | 5.67 | 26.90 | 2.14E−07 | 7.42E−05 |
| ENSG00000094880 | CDC23 | −0.93 | 5.49 | 26.82 | 2.24E−07 | 7.43E−05 |
| ENSG00000161888 | SPC24 | −1.08 | 4.35 | 26.81 | 2.25E−07 | 7.43E−05 |
| ENSG00000066279 | ASPM | −1.18 | 6.89 | 26.71 | 2.36E−07 | 7.62E−05 |
| ENSG00000198901 | PRC1 | −0.91 | 6.85 | 26.11 | 3.23E−07 | 0.000102 |
| ENSG00000088325 | TPX2 | −0.86 | 7.28 | 25.96 | 3.49E−07 | 0.000108 |
| ENSG00000138778 | CENPE | −1.03 | 6.40 | 25.44 | 4.58E−07 | 0.000136 |
| ENSG00000140525 | FANCI | −0.85 | 5.87 | 25.43 | 4.60E−07 | 0.000136 |
| ENSG00000111206 | FOXM1 | −0.80 | 6.61 | 25.29 | 4.94E−07 | 0.000143 |
| ENSG00000076382 | SPAG5 | −0.83 | 5.81 | 25.10 | 5.46E−07 | 0.000155 |
| ENSG00000170312 | CDK1 | −0.95 | 6.03 | 25.05 | 5.59E−07 | 0.000156 |
| ENSG00000161800 | RACGAP1 | −0.88 | 5.47 | 24.90 | 6.04E−07 | 0.000162 |
| ENSG00000168078 | PBK | −0.93 | 5.37 | 24.91 | 6.02E−07 | 0.000162 |
| ENSG00000146072 | TNFRSF21 | 0.88 | 6.42 | 24.77 | 6.45E−07 | 0.00017 |
| ENSG00000134690 | CDCA8 | −1.05 | 5.25 | 24.59 | 7.11E−07 | 0.000184 |
| ENSG00000148773 | MKI67 | −1.17 | 7.99 | 24.06 | 9.33E−07 | 0.000237 |
| ENSG00000102575 | ACP5 | −3.55 | 2.81 | 24.03 | 9.50E−07 | 0.000237 |
| ENSG00000024526 | DEPDC1 | −0.99 | 5.61 | 23.90 | 1.02E−06 | 0.000249 |
| ENSG00000099937 | SERPIND1 | −1.85 | 2.87 | 23.80 | 1.07E−06 | 0.000258 |
| ENSG00000276612 | FP565260.2 | −6.67 | −2.61 | 23.74 | 1.10E−06 | 0.000261 |
| ENSG00000118193 | KIF14 | −1.04 | 5.04 | 23.64 | 1.16E−06 | 0.000266 |
| ENSG00000175063 | UBE2C | −1.03 | 5.18 | 23.65 | 1.16E−06 | 0.000266 |
| ENSG00000123485 | HJURP | −0.92 | 4.98 | 23.46 | 1.28E−06 | 0.000286 |
| ENSG00000157456 | CCNB2 | −0.84 | 5.61 | 23.41 | 1.31E−06 | 0.000286 |
| ENSG00000163584 | RPL22L1 | −0.90 | 5.95 | 23.41 | 1.31E−06 | 0.000286 |
| ENSG00000117724 | CENPF | −0.96 | 7.44 | 22.28 | 2.35E−06 | 0.000506 |
| ENSG00000100297 | MCM5 | −0.86 | 6.30 | 22.12 | 2.56E−06 | 0.000535 |
| ENSG00000105357 | MYH14 | 4.21 | −0.61 | 22.15 | 2.53E−06 | 0.000535 |
| ENSG00000138160 | KIF11 | −0.95 | 6.34 | 22.01 | 2.71E−06 | 0.000558 |
| ENSG00000093009 | CDC45 | −1.00 | 4.55 | 21.97 | 2.77E−06 | 0.000562 |
| ENSG00000185070 | FLRT2 | 0.76 | 8.29 | 21.87 | 2.92E−06 | 0.000584 |
| ENSG00000116774 | OLFML3 | 1.52 | 2.30 | 21.78 | 3.06E−06 | 0.000603 |
| ENSG00000123689 | G0S2 | −1.97 | 2.29 | 21.72 | 3.15E−06 | 0.000613 |
| ENSG00000167900 | TK1 | −0.76 | 5.68 | 21.56 | 3.43E−06 | 0.000655 |
| ENSG00000184661 | CDCA2 | −0.93 | 4.87 | 21.54 | 3.46E−06 | 0.000655 |
| ENSG00000013810 | TACC3 | −0.76 | 6.36 | 21.52 | 3.50E−06 | 0.000655 |
| ENSG00000101057 | MYBL2 | −0.78 | 6.00 | 21.42 | 3.70E−06 | 0.000682 |
| ENSG00000112742 | TTK | −1.03 | 5.14 | 21.29 | 3.95E−06 | 0.000719 |
| ENSG00000163808 | KIF15 | −1.04 | 4.74 | 21.00 | 4.59E−06 | 0.000826 |
| ENSG00000011426 | ANLN | −1.01 | 7.23 | 20.77 | 5.19E−06 | 0.00091 |
| ENSG00000265107 | GJA5 | −6.45 | −2.77 | 20.77 | 5.19E−06 | 0.00091 |
| ENSG00000121152 | NCAPH | −0.96 | 4.79 | 20.73 | 5.28E−06 | 0.000915 |
| ENSG00000114631 | PODXL2 | 1.26 | 3.20 | 20.67 | 5.44E−06 | 0.000932 |
| ENSG00000129173 | E2F8 | −1.04 | 4.57 | 20.50 | 5.97E−06 | 0.00101 |

TABLE 4-continued lists genes differentially expressed in THSD1 knockdown HUVECs
Table 4. Differentially Expressed Genes in THSD1 Knockdown HBMECS

| Ensembl Gene | Gene Symbol | logFC | logCPM | LR | PValue | FDR |
|---|---|---|---|---|---|---|
| ENSG00000101335 | MYL9 | 0.82 | 5.36 | 20.46 | 6.10E−06 | 0.00102 |
| ENSG00000164109 | MAD2L1 | −0.92 | 5.54 | 20.32 | 6.55E−06 | 0.001082 |
| ENSG00000104738 | MCM4 | −0.92 | 6.63 | 20.27 | 6.74E−06 | 0.0011 |
| ENSG00000169679 | BUB1 | −0.99 | 5.93 | 20.11 | 7.32E−06 | 0.001182 |
| ENSG00000073111 | MCM2 | −0.82 | 5.76 | 19.94 | 7.98E−06 | 0.00126 |
| ENSG00000165480 | SKA3 | −0.99 | 4.57 | 19.95 | 7.95E−06 | 0.00126 |
| ENSG00000075218 | GTSE1 | −0.89 | 5.40 | 19.81 | 8.54E−06 | 0.001333 |
| ENSG00000267618 | AC004223.3 | 6.30 | −2.86 | 19.78 | 8.70E−06 | 0.001344 |
| ENSG00000163131 | CTSS | 1.44 | 3.29 | 19.60 | 9.54E−06 | 0.001458 |
| ENSG00000089685 | BIRC5 | −0.77 | 6.29 | 19.52 | 9.98E−06 | 0.001508 |
| ENSG00000178999 | AURKB | −0.98 | 4.85 | 19.36 | 1.08E−05 | 0.001618 |
| ENSG00000186193 | SAPCD2 | −0.87 | 4.80 | 19.32 | 1.10E−05 | 0.001632 |
| ENSG00000071539 | TRIP13 | −0.84 | 5.48 | 19.22 | 1.17E−05 | 0.001707 |
| ENSG00000156504 | FAM122B | −0.84 | 4.71 | 19.18 | 1.19E−05 | 0.001722 |
| ENSG00000165092 | ALDH1A1 | 0.69 | 6.16 | 19.14 | 1.21E−05 | 0.001741 |
| ENSG00000123975 | CKS2 | −0.80 | 5.71 | 19.02 | 1.29E−05 | 0.001764 |
| ENSG00000135476 | ESPL1 | −0.97 | 4.76 | 19.09 | 1.25E−05 | 0.001764 |
| ENSG00000173597 | SULT1B1 | −0.97 | 7.01 | 19.02 | 1.29E−05 | 0.001764 |
| ENSG00000189431 | RASSF10 | −3.28 | −1.94 | 19.03 | 1.29E−05 | 0.001764 |
| ENSG00000237649 | KIFC1 | −0.93 | 5.31 | 19.05 | 1.27E−05 | 0.001764 |
| ENSG00000122966 | CIT | −0.81 | 5.46 | 18.93 | 1.36E−05 | 0.001836 |
| ENSG00000117650 | NEK2 | −0.85 | 4.48 | 18.90 | 1.38E−05 | 0.001846 |
| ENSG00000100526 | CDKN3 | −0.93 | 4.10 | 18.77 | 1.47E−05 | 0.001954 |
| ENSG00000156970 | BUB1B | −0.93 | 5.84 | 18.68 | 1.55E−05 | 0.002039 |
| ENSG00000284041 | AC073111.3 | −6.19 | −2.96 | 18.66 | 1.57E−05 | 0.002041 |
| ENSG00000115163 | CENPA | −1.06 | 3.87 | 18.25 | 1.94E−05 | 0.002507 |
| ENSG00000269891 | ARHGAP19-SLIT1 | 6.14 | −2.97 | 18.05 | 2.15E−05 | 0.002751 |
| ENSG00000065328 | MCM10 | −1.01 | 4.18 | 17.99 | 2.22E−05 | 0.002822 |
| ENSG00000125378 | BMP4 | 0.74 | 6.11 | 17.97 | 2.25E−05 | 0.002823 |
| ENSG00000079616 | KIF22 | −0.75 | 5.65 | 17.89 | 2.35E−05 | 0.002915 |
| ENSG00000151640 | DPYSL4 | 0.98 | 4.09 | 17.87 | 2.36E−05 | 0.002915 |
| ENSG00000053747 | LAMA3 | −0.87 | 4.23 | 17.67 | 2.62E−05 | 0.003214 |
| ENSG00000154175 | ABI3BP | −0.84 | 5.18 | 17.65 | 2.65E−05 | 0.003219 |
| ENSG00000183856 | IQGAP3 | −0.81 | 5.10 | 17.63 | 2.68E−05 | 0.003226 |
| ENSG00000198826 | ARHGAP11A | −0.92 | 6.08 | 17.48 | 2.91E−05 | 0.003475 |
| ENSG00000228716 | DHFR | −0.74 | 6.16 | 17.44 | 2.97E−05 | 0.003512 |
| ENSG00000076003 | MCM6 | −0.84 | 6.10 | 17.39 | 3.05E−05 | 0.003576 |
| ENSG00000173166 | RAPH1 | −0.94 | 5.58 | 17.28 | 3.22E−05 | 0.003754 |
| ENSG00000123473 | STIL | −0.90 | 4.92 | 17.23 | 3.31E−05 | 0.003819 |
| ENSG00000117595 | IRF6 | 1.52 | 3.34 | 17.10 | 3.55E−05 | 0.004062 |
| ENSG00000146918 | NCAPG2 | −0.77 | 5.94 | 17.06 | 3.63E−05 | 0.004089 |
| ENSG00000164647 | STEAP1 | −0.83 | 5.07 | 17.07 | 3.61E−05 | 0.004089 |
| ENSG00000196878 | LAMB3 | −0.85 | 4.47 | 17.03 | 3.67E−05 | 0.004108 |
| ENSG00000171241 | SHCBP1 | −0.86 | 5.58 | 17.01 | 3.72E−05 | 0.004126 |
| ENSG00000150630 | VEGFC | −0.96 | 4.78 | 16.89 | 3.95E−05 | 0.004353 |
| ENSG00000090889 | KIF4A | −0.77 | 5.75 | 16.62 | 4.56E−05 | 0.004974 |
| ENSG00000121621 | KIF18A | −0.92 | 4.27 | 16.61 | 4.59E−05 | 0.004974 |
| ENSG00000101447 | FAM83D | −0.88 | 5.40 | 16.54 | 4.77E−05 | 0.005136 |
| ENSG00000169604 | ANTXR1 | 1.03 | 4.62 | 16.47 | 4.93E−05 | 0.005267 |
| ENSG00000096060 | FKBP5 | −0.68 | 6.90 | 16.31 | 5.38E−05 | 0.005672 |
| ENSG00000167434 | CA4 | −4.19 | −2.69 | 16.31 | 5.39E−05 | 0.005672 |
| ENSG00000163092 | XIRP2 | 1.93 | 1.44 | 16.29 | 5.43E−05 | 0.005675 |
| ENSG00000104147 | OIP5 | −1.14 | 2.91 | 16.25 | 5.56E−05 | 0.005762 |
| ENSG00000119403 | PHF19 | −0.64 | 6.01 | 16.19 | 5.74E−05 | 0.005868 |
| ENSG00000211448 | DIO2 | 1.64 | 0.55 | 16.20 | 5.71E−05 | 0.005868 |
| ENSG00000185432 | METTL7A | −0.90 | 5.20 | 16.11 | 5.99E−05 | 0.006078 |
| ENSG00000105499 | PLA2G4C | 1.03 | 3.47 | 16.09 | 6.05E−05 | 0.006091 |
| ENSG00000139734 | DIAPH3 | −0.80 | 5.47 | 16.01 | 6.30E−05 | 0.0063 |
| ENSG00000163453 | IGFBP7 | 0.68 | 7.65 | 15.92 | 6.60E−05 | 0.006561 |
| ENSG00000140416 | TPM1 | 0.64 | 8.27 | 15.87 | 6.77E−05 | 0.006677 |
| ENSG00000109805 | NCAPG | −0.77 | 6.26 | 15.73 | 7.30E−05 | 0.007153 |
| ENSG00000137807 | KIF23 | −0.78 | 5.95 | 15.66 | 7.59E−05 | 0.007335 |
| ENSG00000179195 | ZNF664 | −0.88 | 6.90 | 15.66 | 7.58E−05 | 0.007335 |
| ENSG00000144554 | FANCD2 | −0.87 | 4.59 | 15.57 | 7.95E−05 | 0.007632 |
| ENSG00000101003 | GINS1 | −0.83 | 4.79 | 15.51 | 8.19E−05 | 0.007811 |
| ENSG00000137310 | TCF19 | −0.81 | 4.92 | 15.35 | 8.92E−05 | 0.008445 |
| ENSG00000115008 | IL1A | 1.97 | 0.90 | 15.32 | 9.06E−05 | 0.008525 |
| ENSG00000163751 | CPA3 | 1.34 | 1.70 | 15.30 | 9.18E−05 | 0.008576 |
| ENSG00000197632 | SERPINB2 | −1.60 | 3.06 | 15.21 | 9.61E−05 | 0.008924 |
| ENSG00000133119 | RFC3 | −0.80 | 4.52 | 15.16 | 9.87E−05 | 0.009103 |
| ENSG00000140545 | MFGE8 | 0.73 | 5.90 | 15.12 | 0.00010086 | 0.009244 |
| ENSG00000101188 | NTSR1 | −1.16 | 2.79 | 15.08 | 0.00010312 | 0.009391 |
| ENSG00000171848 | RRM2 | −1.18 | 6.87 | 15.06 | 0.00010394 | 0.009404 |
| ENSG00000185480 | PARPBP | −0.79 | 4.44 | 15.05 | 0.00010467 | 0.009411 |

TABLE 4-continued lists genes differentially expressed in THSD1 knockdown HUVECs
Table 4. Differentially Expressed Genes in THSD1 Knockdown HBMECS

| Ensembl Gene | Gene Symbol | logFC | logCPM | LR | PValue | FDR |
| --- | --- | --- | --- | --- | --- | --- |
| ENSG00000140675 | SLC5A2 | 4.89 | −2.99 | 14.82 | 0.00011808 | 0.010484 |
| ENSG00000151725 | CENPU | −0.74 | 4.67 | 14.83 | 0.00011777 | 0.010484 |
| ENSG00000168243 | GNG4 | 2.60 | −1.74 | 14.78 | 0.00012062 | 0.010643 |
| ENSG00000173207 | CKS1B | −0.73 | 5.38 | 14.77 | 0.0001214 | 0.010646 |
| ENSG00000010292 | NCAPD2 | −0.62 | 7.04 | 14.64 | 0.00012988 | 0.011319 |
| ENSG00000173281 | PPP1R3B | 0.64 | 6.98 | 14.61 | 0.0001319 | 0.011425 |
| ENSG00000164611 | PTTG1 | −0.64 | 5.60 | 14.58 | 0.00013445 | 0.011569 |
| ENSG00000167261 | DPEP2 | 2.79 | −2.01 | 14.57 | 0.00013518 | 0.011569 |
| ENSG00000184445 | KNTC1 | −0.70 | 5.37 | 14.55 | 0.00013641 | 0.011604 |
| ENSG00000012048 | BRCA1 | −0.90 | 4.77 | 14.49 | 0.00014056 | 0.011791 |
| ENSG00000092853 | CLSPN | −0.87 | 4.95 | 14.49 | 0.0001411 | 0.011791 |
| ENSG00000203668 | CHML | −0.70 | 5.13 | 14.49 | 0.00014087 | 0.011791 |
| ENSG00000101868 | POLA1 | −0.84 | 4.68 | 14.45 | 0.00014375 | 0.011893 |
| ENSG00000122694 | GLIPR2 | 0.70 | 5.12 | 14.45 | 0.000144 | 0.011893 |
| ENSG00000149591 | TAGLN | 1.24 | 1.91 | 14.37 | 0.00015051 | 0.012359 |
| ENSG00000280537 | AC068946.1 | 2.14 | −1.15 | 14.35 | 0.00015184 | 0.012397 |
| ENSG00000105011 | ASF1B | −0.91 | 4.72 | 14.28 | 0.00015721 | 0.012762 |
| ENSG00000105889 | STEAP1B | −0.83 | 4.64 | 14.20 | 0.00016442 | 0.013271 |
| ENSG00000124721 | DNAH8 | 1.61 | 3.82 | 14.17 | 0.00016717 | 0.013341 |
| ENSG00000130816 | DNMT1 | −0.60 | 7.04 | 14.17 | 0.00016671 | 0.013341 |
| ENSG00000162645 | GBP2 | 0.60 | 6.15 | 14.14 | 0.00016943 | 0.013447 |
| ENSG00000058804 | NDC1 | −0.71 | 5.97 | 14.03 | 0.00018026 | 0.014227 |
| ENSG00000145604 | SKP2 | −0.67 | 5.33 | 14.00 | 0.0001825 | 0.014324 |
| ENSG00000123219 | CENPK | −0.71 | 4.81 | 13.98 | 0.00018513 | 0.014341 |
| ENSG00000136824 | SMC2 | −0.81 | 6.08 | 13.97 | 0.00018575 | 0.014341 |
| ENSG00000188517 | COL25A1 | 2.38 | −1.61 | 13.97 | 0.00018564 | 0.014341 |
| ENSG00000107984 | DKK1 | −0.63 | 5.85 | 13.95 | 0.00018762 | 0.01437 |
| ENSG00000204262 | COL5A2 | 0.61 | 8.73 | 13.95 | 0.00018814 | 0.01437 |
| ENSG00000162063 | CCNF | −0.67 | 5.31 | 13.89 | 0.00019352 | 0.014701 |
| ENSG00000258064 | AC073612.1 | −6.56 | −2.69 | 13.76 | 0.00020816 | 0.01573 |
| ENSG00000120802 | TMPO | −0.66 | 7.44 | 13.64 | 0.00022161 | 0.016569 |
| ENSG00000163507 | CIP2A | −0.82 | 5.14 | 13.64 | 0.0002212 | 0.016569 |
| ENSG00000186185 | KIF18B | −0.86 | 4.35 | 13.61 | 0.00022501 | 0.016735 |
| ENSG00000149503 | INCENP | −0.86 | 5.22 | 13.41 | 0.00025051 | 0.018535 |
| ENSG00000167601 | AXL | −0.55 | 7.33 | 13.28 | 0.00026806 | 0.019731 |
| ENSG00000139618 | BRCA2 | −0.91 | 4.49 | 13.19 | 0.00028185 | 0.020639 |
| ENSG00000163554 | SPTA1 | 2.18 | −0.67 | 13.16 | 0.00028663 | 0.020881 |
| ENSG00000100311 | PDGFB | 0.82 | 6.70 | 13.08 | 0.00029782 | 0.021586 |
| ENSG00000106069 | CHN2 | 0.94 | 3.27 | 12.98 | 0.00031547 | 0.022542 |
| ENSG00000239389 | PCDHA13 | 6.39 | −2.80 | 12.99 | 0.00031302 | 0.022542 |
| ENSG00000258947 | TUBB3 | 0.59 | 7.10 | 12.97 | 0.00031577 | 0.022542 |
| ENSG00000144354 | CDCA7 | −0.74 | 4.99 | 12.94 | 0.0003212 | 0.022815 |
| ENSG00000123080 | CDKN2C | −0.81 | 4.00 | 12.93 | 0.00032414 | 0.022909 |
| ENSG00000103489 | XYLT1 | 1.13 | 2.69 | 12.83 | 0.00034094 | 0.023859 |
| ENSG00000178538 | CA8 | −1.71 | 0.71 | 12.83 | 0.00034088 | 0.023859 |
| ENSG00000163535 | SGO2 | −0.80 | 5.30 | 12.81 | 0.00034481 | 0.024012 |
| ENSG00000133110 | POSTN | −1.11 | 3.05 | 12.78 | 0.00035075 | 0.024306 |
| ENSG00000035499 | DEPDC1B | −0.85 | 4.24 | 12.75 | 0.00035616 | 0.024325 |
| ENSG00000150540 | HNMT | 0.80 | 4.05 | 12.75 | 0.0003557 | 0.024325 |
| ENSG00000176890 | TYMS | −0.61 | 6.99 | 12.75 | 0.00035522 | 0.024325 |
| ENSG00000261459 | AC002310.5 | −6.20 | −2.95 | 12.71 | 0.00036311 | 0.024681 |
| ENSG00000117593 | DARS2 | −0.67 | 5.54 | 12.68 | 0.00036955 | 0.024999 |
| ENSG00000111341 | MGP | −0.57 | 6.67 | 12.65 | 0.00037599 | 0.025314 |
| ENSG00000058085 | LAMC2 | 0.75 | 4.73 | 12.57 | 0.00039222 | 0.026282 |
| ENSG00000103257 | SLC7A5 | −0.71 | 4.74 | 12.49 | 0.00040895 | 0.027275 |
| ENSG00000214357 | NEURL1B | −1.41 | 0.86 | 12.46 | 0.0004151 | 0.027556 |
| ENSG00000258555 | SPECC1L-ADORA2A | 6.16 | −2.96 | 12.37 | 0.00043612 | 0.028683 |
| ENSG00000268643 | AC006486.1 | −6.10 | −3.02 | 12.37 | 0.00043584 | 0.028683 |
| ENSG00000186871 | ERCC6L | −0.97 | 3.80 | 12.31 | 0.00045156 | 0.029562 |
| ENSG00000128944 | KNSTRN | −0.64 | 5.27 | 12.26 | 0.00046273 | 0.029611 |
| ENSG00000134222 | PSRC1 | −0.89 | 3.87 | 12.28 | 0.00045803 | 0.029611 |
| ENSG00000142731 | PLK4 | −0.89 | 4.91 | 12.27 | 0.00046122 | 0.029611 |
| ENSG00000147536 | GINS4 | −0.85 | 4.14 | 12.28 | 0.00045741 | 0.029611 |
| ENSG00000267022 | AC067968.1 | −2.73 | −1.12 | 12.26 | 0.00046177 | 0.029611 |
| ENSG00000155093 | PTPRN2 | 1.40 | 0.73 | 12.23 | 0.00047029 | 0.029846 |
| ENSG00000188229 | TUBB4B | −0.69 | 8.39 | 12.23 | 0.00047061 | 0.029846 |
| ENSG00000215252 | GOLGA8B | 0.68 | 4.46 | 12.21 | 0.00047536 | 0.030013 |
| ENSG00000149573 | MPZL2 | −0.67 | 5.40 | 12.20 | 0.00047877 | 0.030095 |
| ENSG00000129195 | PIMREG | −0.79 | 4.07 | 12.18 | 0.00048388 | 0.030282 |
| ENSG00000152104 | PTPN14 | −0.60 | 7.17 | 12.16 | 0.00048777 | 0.030391 |
| ENSG00000197457 | STMN3 | 2.81 | 3.31 | 12.14 | 0.00049373 | 0.030629 |
| ENSG00000168874 | ATOH8 | 0.84 | 3.70 | 12.13 | 0.00049593 | 0.030631 |
| ENSG00000255073 | ZFP91-CNTF | −5.43 | −3.45 | 12.10 | 0.00050547 | 0.031085 |
| ENSG00000188486 | H2AFX | −0.63 | 6.27 | 12.02 | 0.00052646 | 0.032209 |

TABLE 4-continued lists genes differentially expressed in THSD1 knockdown HUVECs
Table 4. Differentially Expressed Genes in THSD1 Knockdown HBMECS

| Ensembl Gene | Gene Symbol | logFC | logCPM | LR | PValue | FDR |
|---|---|---|---|---|---|---|
| ENSG00000213297 | ZNF625-ZNF20 | 1.41 | 0.93 | 12.01 | 0.00052828 | 0.032209 |
| ENSG00000102007 | PLP2 | −0.55 | 6.27 | 11.97 | 0.00053967 | 0.032496 |
| ENSG00000135842 | FAM129A | −1.02 | 3.29 | 11.97 | 0.00053985 | 0.032496 |
| ENSG00000168843 | FSTL5 | 1.09 | 3.04 | 11.98 | 0.00053834 | 0.032496 |
| ENSG00000178878 | APOLD1 | −0.89 | 3.58 | 11.94 | 0.00055082 | 0.033017 |
| ENSG00000113368 | LMNB1 | −0.66 | 6.70 | 11.92 | 0.00055512 | 0.033135 |
| ENSG00000137473 | TTC29 | 1.72 | −0.20 | 11.88 | 0.0005664 | 0.033666 |
| ENSG00000148848 | ADAM12 | 1.25 | 1.79 | 11.86 | 0.00057272 | 0.0339 |
| ENSG00000114346 | ECT2 | −0.68 | 5.97 | 11.84 | 0.00058063 | 0.034226 |
| ENSG00000196739 | COL27A1 | 0.57 | 5.97 | 11.77 | 0.00060245 | 0.03522 |
| ENSG00000258677 | AC022826.2 | −1.79 | −0.91 | 11.77 | 0.00060175 | 0.03522 |
| ENSG00000129810 | SGO1 | −0.89 | 3.52 | 11.75 | 0.00060846 | 0.035425 |
| ENSG00000198830 | HMGN2 | −0.53 | 8.42 | 11.73 | 0.00061337 | 0.035566 |
| ENSG00000174371 | EXO1 | −0.93 | 3.73 | 11.69 | 0.00062871 | 0.036307 |
| ENSG00000127564 | PKMYT1 | −0.90 | 3.52 | 11.66 | 0.00063706 | 0.03664 |
| ENSG00000100368 | CSF2RB | 0.55 | 5.77 | 11.64 | 0.00064394 | 0.036738 |
| ENSG00000135451 | TROAP | −0.73 | 4.10 | 11.64 | 0.00064385 | 0.036738 |
| ENSG00000092470 | WDR76 | −0.72 | 4.40 | 11.60 | 0.00065967 | 0.037485 |
| ENSG00000143401 | ANP32E | −0.56 | 6.78 | 11.58 | 0.00066731 | 0.037768 |
| ENSG00000257411 | AC034102.2 | 1.93 | 0.75 | 11.54 | 0.0006809 | 0.038384 |
| ENSG00000146670 | CDCA5 | −0.72 | 5.02 | 11.50 | 0.00069768 | 0.039175 |
| ENSG00000167325 | RRM1 | −0.57 | 6.89 | 11.47 | 0.00070846 | 0.039623 |
| ENSG00000152253 | SPC25 | −0.89 | 3.82 | 11.46 | 0.00071221 | 0.039677 |
| ENSG00000122952 | ZWINT | −0.71 | 5.53 | 11.43 | 0.00072353 | 0.04015 |
| ENSG00000121966 | CXCR4 | 1.02 | 5.44 | 11.40 | 0.00073256 | 0.040493 |
| ENSG00000101224 | CDC25B | −0.56 | 6.33 | 11.38 | 0.00074161 | 0.040707 |
| ENSG00000136490 | LIMD2 | 0.60 | 5.23 | 11.38 | 0.00074216 | 0.040707 |
| ENSG00000127528 | KLF2 | −0.82 | 4.46 | 11.35 | 0.00075267 | 0.041125 |
| ENSG00000151388 | ADAMTS12 | 0.85 | 3.45 | 11.34 | 0.00075879 | 0.041163 |
| ENSG00000154839 | SKA1 | −0.87 | 4.20 | 11.34 | 0.00075917 | 0.041163 |
| ENSG00000119969 | HELLS | −0.65 | 4.77 | 11.30 | 0.00077592 | 0.041911 |
| ENSG00000108055 | SMC3 | −0.53 | 6.68 | 11.28 | 0.00078172 | 0.042065 |
| ENSG00000125695 | AC046185.1 | 5.80 | −3.20 | 11.24 | 0.00079891 | 0.042828 |
| ENSG00000146411 | SLC2A12 | 1.26 | 2.09 | 11.23 | 0.00080506 | 0.042888 |
| ENSG00000159167 | STC1 | −0.93 | 4.54 | 11.23 | 0.00080607 | 0.042888 |
| ENSG00000181634 | TNFSF15 | 0.78 | 5.81 | 11.19 | 0.00082212 | 0.043579 |
| ENSG00000111665 | CDCA3 | −0.78 | 3.97 | 11.16 | 0.00083518 | 0.044106 |
| ENSG00000067141 | NEO1 | −2.49 | −2.06 | 11.10 | 0.00086297 | 0.045237 |
| ENSG00000099282 | TSPAN15 | 0.66 | 6.21 | 11.10 | 0.00086289 | 0.045237 |
| ENSG00000120256 | LRP11 | 0.57 | 5.86 | 10.97 | 0.00092765 | 0.048365 |
| ENSG00000145990 | GFOD1 | −0.59 | 5.47 | 10.96 | 0.00093285 | 0.048365 |
| ENSG00000166250 | CLMP | −1.02 | 2.47 | 10.96 | 0.00093028 | 0.048365 |
| ENSG00000072501 | SMC1A | −0.59 | 6.94 | 10.94 | 0.00093894 | 0.048504 |
| ENSG00000112378 | PERP | −0.59 | 7.18 | 10.92 | 0.00095053 | 0.048925 |
| ENSG00000077152 | UBE2T | −0.67 | 4.49 | 10.90 | 0.00096365 | 0.049243 |
| ENSG00000198553 | KCNRG | 1.57 | −0.55 | 10.90 | 0.00096042 | 0.049243 |
| ENSG00000120337 | TNFSF18 | 0.87 | 4.84 | 10.87 | 0.00097964 | 0.049881 |

Bioinformatic analyses highlighted a potential role for the Src Signaling pathway, and other pathways, in the pathology of IA. We evaluated the potential link to the Src signaling pathway below.

Example 2: THSD1 Negatively Regulates Autophagy, which Impairs Cerebrovascular Integrity and Contributes to IA Development Intracranial aneurysm (IA) is a weakened area in the wall of cerebral artery that leads to a bulging in a brain blood vessel. The rupture of IA causes aneurysmal subarachnoid hemorrhage (SAH), a devastating form of stroke. More than 30% will die due to SAH and more than half of survivors will never return to independent living. Unfortunately, there are no treatments for IA except open or endovascular surgery. Attempts to find new therapeutic avenues are greatly hindered by the lack of knowledge of the gene(s) and pathways responsible for IA development and growth.

Autophagy is a catabolic process that degrades intracellular cargos. The autophagosome, a double membrane-bound vesicle with LC3 protein associated on both sides, engulfs cytoplasmic constituents and later fuses with lysosome for degradation. In comparison to starvation-induced bulk autophagy, selective autophagy plays an important role in controlling organelle homeostasis. Although it is believed that SRC kinase promotes the direct interaction of LC3 and paxillin in a phosphorylation-dependent manner, the upstream signaling that determines the temporospatial degradation of FA remains unclear. The disclosure contemplates that THSD1 is the upstream regulator of the selective autophagy cascade in endothelial cells and that the THSD1-autophagy-FA axis regulates cerebrovascular integrity, and this is impaired in IA patients.

Materials and Methods

Cell Culture

HEK293T cells were maintained in DMEM medium (Corning, 10-013-CV) containing 10% fetal bovine serum (Invitrogen, 10082147), 100 IU penicillin, and 100 μg/ml streptomycin. Transfections of small interfering RNAs and plasmid DNA were performed using lipofectamine 2000 (Life Technologies, 11668027) according to the manufacturer's instructions. Alternatively, for cells such as endothelial cells that are hard to transfect, we will utilize lentiviral system to generate stable cell lines.

Western Blot

Cells were lysed in 1% Triton lysis buffer and sonicated briefly before centrifuged at 18506 g for 30 min at 4° C. Total cell lysates were added by 2×SDS sample buffer and then subjected to discontinuous SDS-PAGE analysis. Proteins were transferred to nitro-cellulose membranes using a Bio-Rad (Hercules, CA) mini transfer apparatus followed by blocking with 5% nonfat milk. Primary antibodies and secondary antibodies were used usually at 1:1000 and 1:10000 dilutions respectively before using an Odyssey system to detect the fluorescence signal.

Immunofluorescence

Cells were grown on glass coverslips in the DMEM medium for 16 h before fixed with 4% formaldehyde-phosphate-buffered saline (Electronic Microscopy Sciences, 15710; Fisher Scientific, BP399-500) for 10 min. Cells were incubated with primary antibodies against focal adhesion markers such as paxillin overnight at 4° C. after 1 h blocking by 5% goat serum. Secondary antibodies conjugated with Alexa Fluor 488 or 594 were used to visualize the localization. Image was taken with a Leica Confocal Microscope and processed by ImageJ and GraphPad 7 software for statistical analysis.

Intracranial Hemorrhage in Zebrafish

Anti-sense morpholinos against thsd1, atg5 or talin was injected into one-cell stage zebrafish singly or in combination to silence the gene accordingly. At day 2 to day 3, embryos will be checked under regular optical microscope. Embryos with intracranial hemorrhages will be counted and imaged by Olympus microscope.

MicroFil Injection in Mice

Prepare MicroFil (Flow Tech, Inc. Carver, MA) casting solution according to the manufacturer's instruction: Mix 5 ml of MV diluent with 4 ml of filtered MV-112 compound (yellow). Add 450 μl (5%) of catalyst (MV curing agent). Use 10 ml syringe to inject MicroFil mixture into the left ventricle after the blood was flushed out by saline. Inject MicroFil mixture slowly into the left ventricle at approximately 3 ml/min.

En Face Immunostaining of Circle of Willis in Mice

For en face immunostaining, isolated intracerebral arteries were dissected out from the brain with micro-needle and micro-scissors under the stereomicroscope. For immunofluorescent staining, tissue samples were washed in phosphate buffered saline (PBS), blocked with 5% goat scrum in PBST (0.1% Triton-X in PBS), then incubated with primary antibodies followed by the appropriate fluorescent-labeled secondary antibodies.

The IA-causing gene THSD1 is required for focal adhesion stability.

Figure 3:
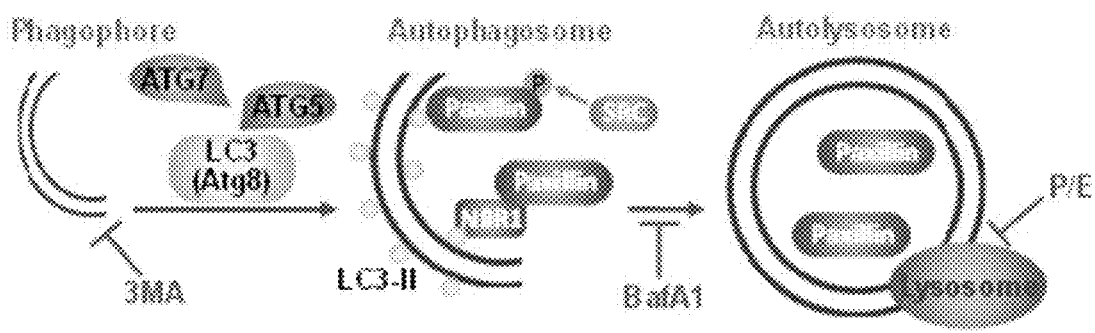
FIG. 3 (FIG. 3) is a drawing depicting a model of autophagy pathway that degrades focal adhesion.

The present disclosure contemplates that THSD1 may be a new endothelial-specific, mechanosensory protein that regulates autophagy pathway. FIG. 3 is a schematic model of autophagy pathway for focal adhesion degradation. Autophagy related genes (ATGx) are highlighted in black letters; drugs that inhibit different stages of autophagy are highlighted in red. Paxillin is a marker for focal adhesion. Out of the exemplary drugs depicted in FIG. 3. 3-Methyladenine (3-MA) is used to inhibit and study the mechanism of autophagy (lysosomal self-degradation) and apoptosis under various conditions. 3-MA inhibits autophagy by blocking autophagosome formation via the inhibition of type III Phosphatidylinositol 3-kinases (PI-3K). Bafilomycin A1 (BafA1), a macrolide antibiotic, is a known inhibitor of the latter stages of autophagy, inhibiting fusion between autophagosomes and lysosomes by inhibiting vacuolar H+ ATPase. P/E refers to Pepstatin A and E-64-d. Both are lysosome protease inhibitors.

Autophagy activity impairs cerebrovascular integrity and promotes IA formation, likely via destabilization of focal adhesion.

Figure 4A:
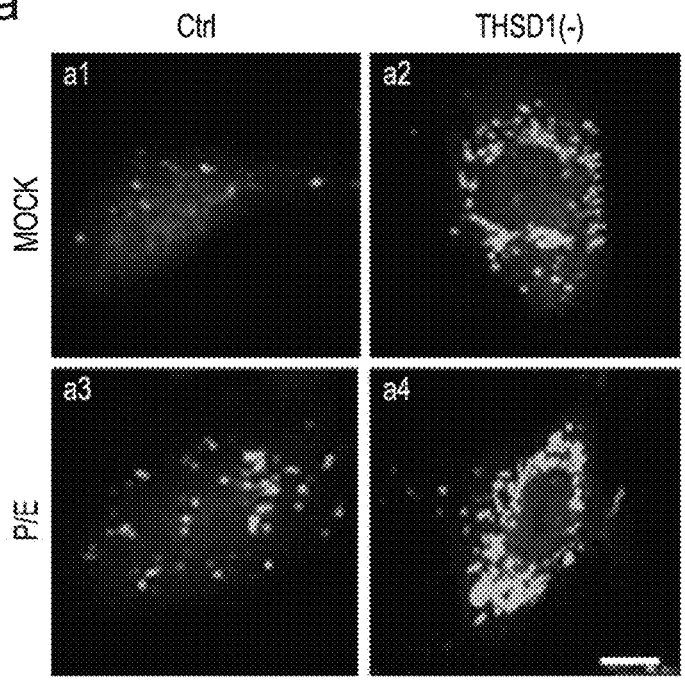
FIG. 4a through FIG. 4f (FIG. 4a-4f) are experimental results depicting that loss-of-function of THSD1 activates endothelial autophagy. Legend: P/E: Pepstatin A and E-64-d.
Figure 4B:
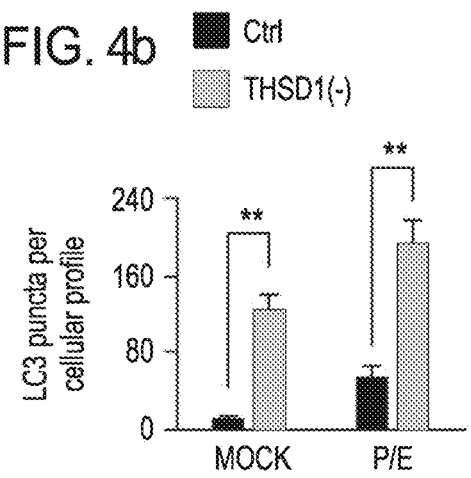
Figure 4C:
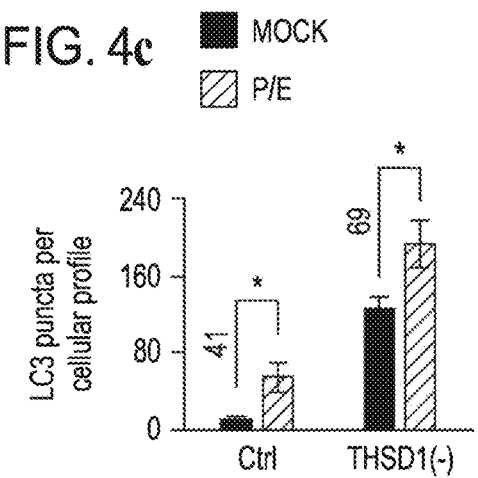
Figure 4D:
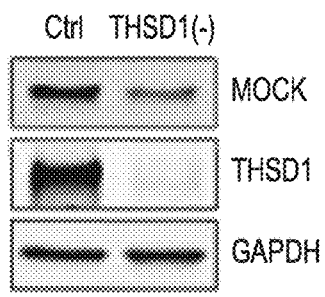
Figure 4E:
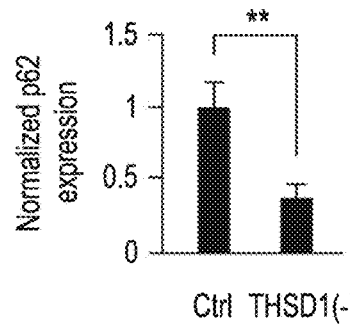
Figure 4F:
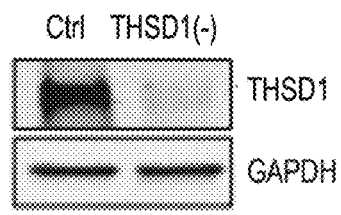

To evaluate the molecular effect of THSD1 on endothelial autophagy signaling activity in human tissue samples the level of LC3 lipidation and p62 turnover were measured with Western blot and immunostaining in THSD1-deficient endothelial cells, so as to predict the IA progression and rupture. Collectively. FIGS. 4a-4f illustrate increased LC3 puncta formation and reduced p62 level in THSD1-deficient endothelial cells. Representative images of GFP-LC3 puncta formation (FIG. 4a) and quantification (FIG. 4b) upon THSD1 knockdown are shown. The flux value is calculated as the difference imposed by P/E treatment (FIG. 4c). The level of p62 (FIG. 4d) is detected by western and quantified in (FIG. 4e). THSD1 knockdown efficiency is confirmed by western in (FIG. 4f). *P<0.05 and **P<0.01. Scale bar: 10 mm.

Collectively. FIGS. 5a-5b demonstrate that autophagy inhibition rescues focal adhesion defects in human THSD1-deficient endothelial cells. Representative images of FA indicated by co-staining of paxillin (green) and actin (red) upon THSD1 and/or ATG5 knockdown are shown in (FIG. 4a) and quantified in (FIG. 4b). **P<0.01. Scale bar: 5 mm. As shown in FIGS. 5a-5b. ATG5 knockdown rescues defective FA in THSD1-deficient primary endothelial cells.

Conclusion

These result support that the IA-causing gene THSD1 negatively regulates autophagy pathway in human cells. This raises a novel concept that autophagy may play a pathogenic role in IA disease.

Example 3: In-Vivo Autophagy Inhibition Rescues Cerebrovascular Integrity Defects In-Vivo Zebrafish Model Intracranial aneurysm and hemorrhage are tightly associated with compromised cerebrovascular integrity. Recently, zebrafish have gained additional popularity as a vertebrate model organism for studying the cerebrovasculature. Since zebrafish embryos are transparent, intracranial hemorrhage can be directly observed using a standard microscope. Furthermore, zebrafish fecundity and rapid development permits rapid phenotypic evaluation as intracranial hemorrhage in zebrafish fry are detectable as early as 2-3 days post fertilization. Importantly, gain-of-function and loss-of-function approaches are well established in zebrafish that include morpholino and mRNA injections and more recently, through applications of CRISPR/Cas9 technology.

Figure 6A:
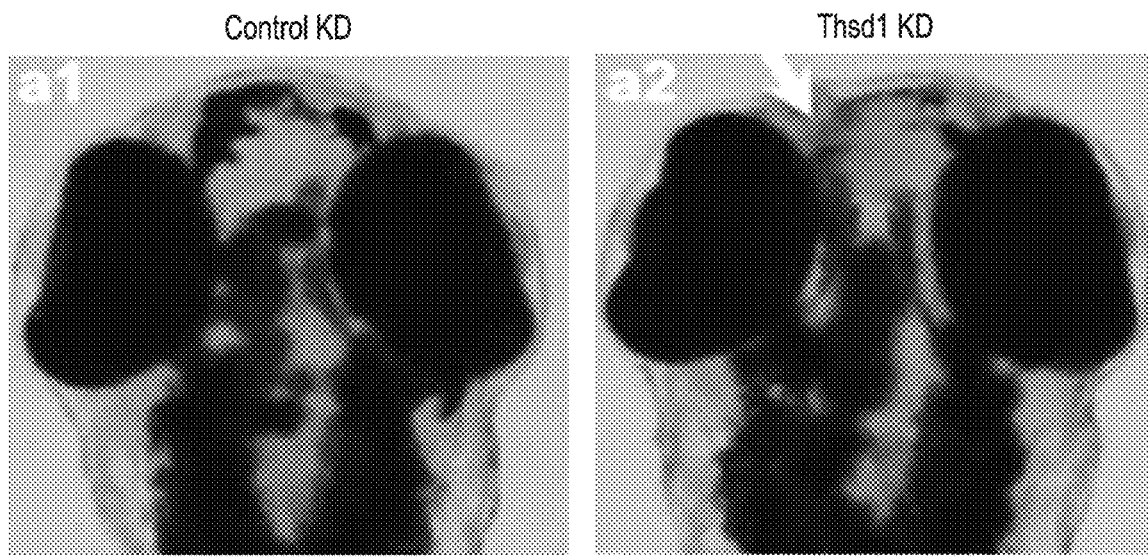
FIG. 6a through FIG. 6c (FIG. 6a-6c) are experimental results depicting that autophagy inhibition rescues cerebrovascular integrity defects in Thsd1-deficient zebrafish.
Figure 6B:
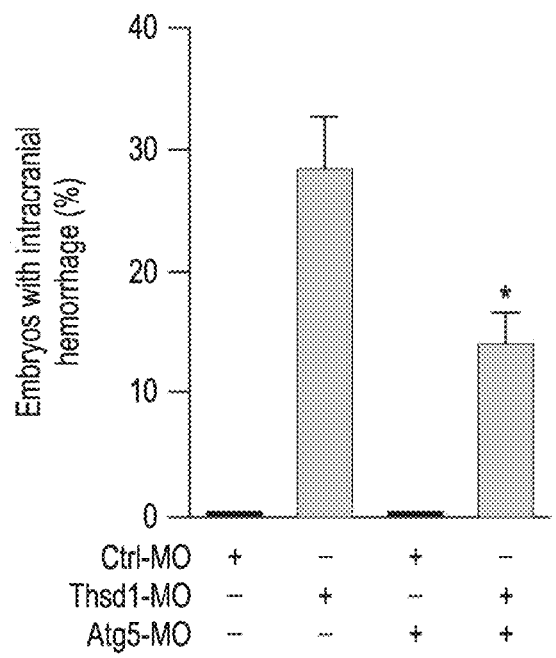
Figure 6C:
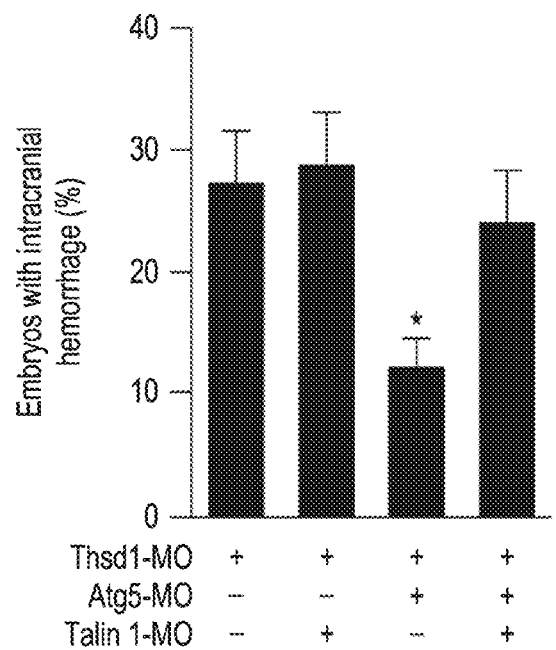

Collectively, FIGS. 6a-6c demonstrate that autophagy inhibition rescues cerebrovascular integrity defects in an in-vivo model, namely Thsd1-deficient zebrafish. FIGS. 6a-6c show that knockdown of atg5 rescues intracranial hemorrhage in Thsd1-deficient zebrafish. A prominent cerebral hemorrhage phenotype was observed in thsd1 knockdown zebrafish (FIG. 6a). Atg5 knockdown ameliorated Thsd1-dependent hemorrhage incidents (comparing grey bars in FIG. 6b), which was prohibited by further knockdown of talin I (comparing the third and fourth bar in FIG. 6c). For each MO injection, 76-92 embryos were analyzed. *p<0.05.

In-Vivo Mammalian Model

Figure 7:
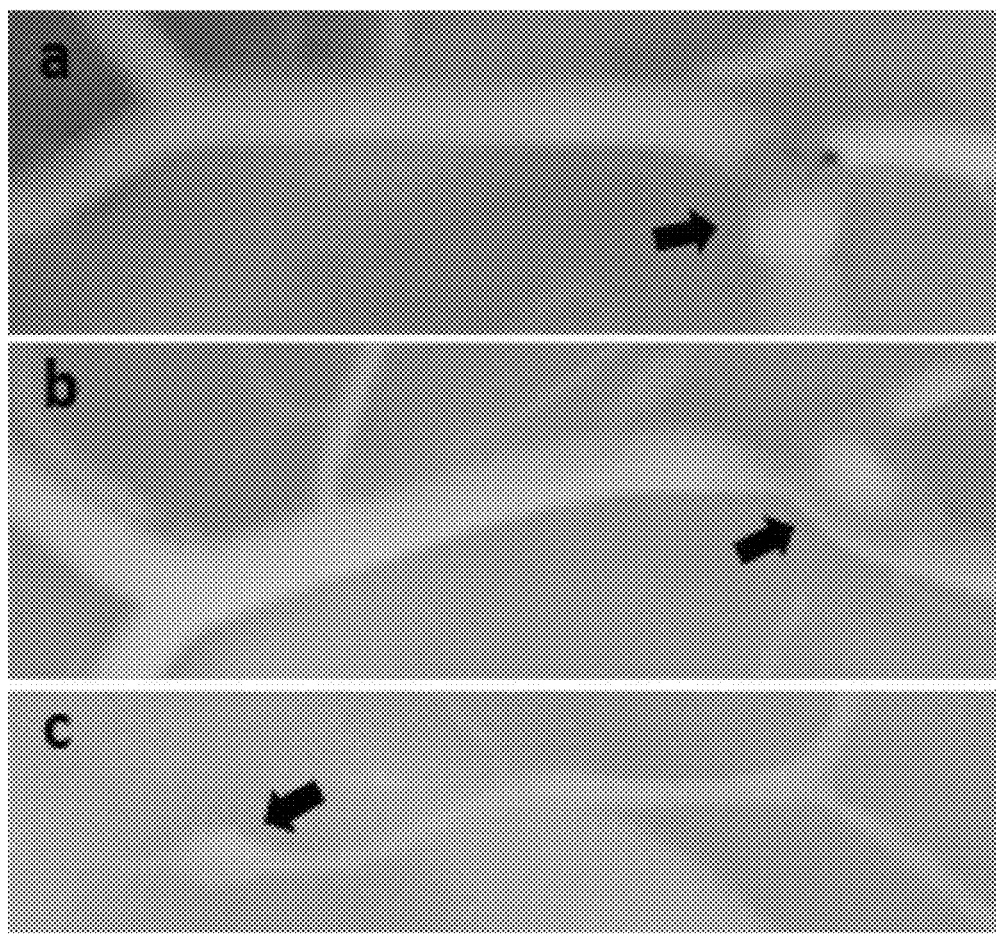
FIG. 7 (FIG. 7) are experimental results depicting that loss-of-function of Thsd1 promotes IA formation in circle of Willis in mice.

To interrogate the consequence of Thsd1 loss in mammals, we used the Thsd1 knockout mouse that contains a knockin of a fluorescent Venus reporter. Thsd1$^{Venus/+}$ and Thsd1$^{Venus/Venus}$ mice survived to weaning age in expected Mendelian ratios. However, brain magnetic resonance imagings revealed mild to severe dilatation of cerebral ventricles, consistent with hydrocephalus in a subset of mutant mice as young as 8 weeks (not shown here, previously reported). FIG. 7 illustrates that loss-of-function of Thsd1 promotes IA formation in circle of Willis in mice. FIG. 7 shows that IAs were visualized by Microfil including a PCA (top), a left Pcom (middle), and a right ICA (bottom) as indicated by arrows. n=10.

Figure 8A:
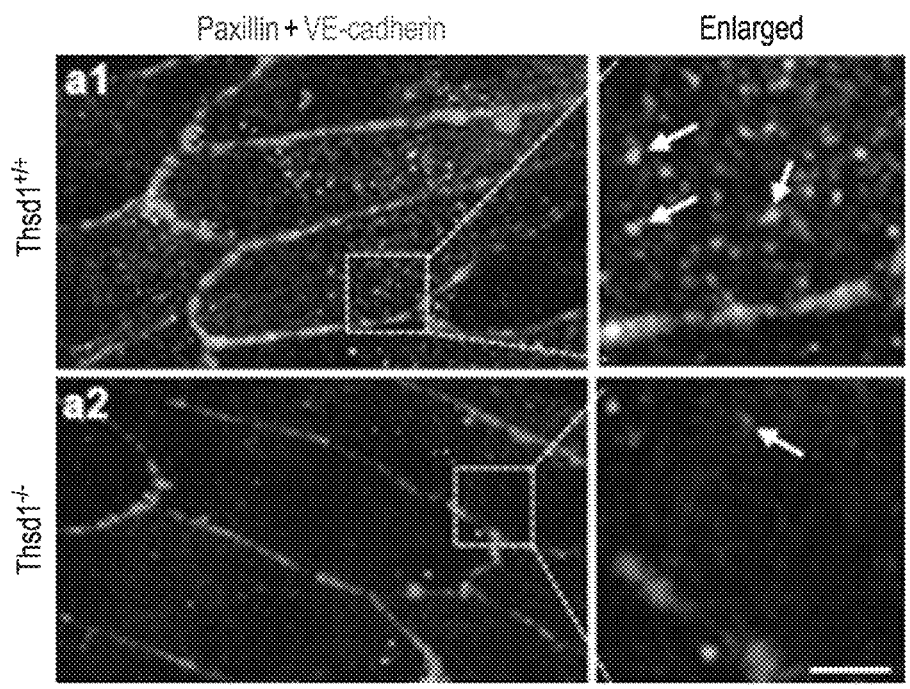
FIG. 8a through FIG. 8c (FIG. 8a-8c) are experimental results depicting that loss-of-function of Thsd1 reduces FA number in intimal endothelial cells in circle of Willis in mice.
Figure 8B:
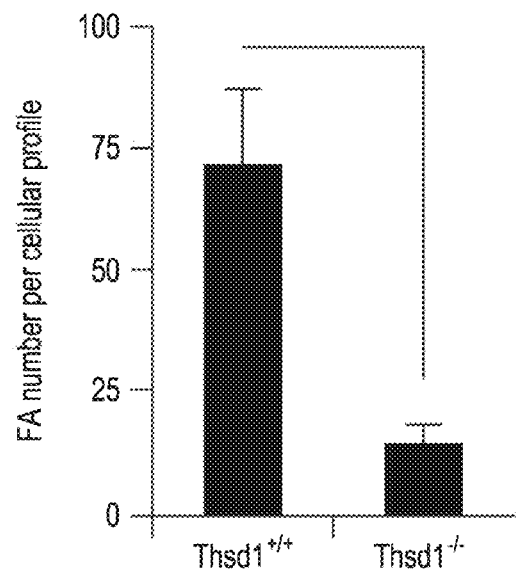
Figure 8C:
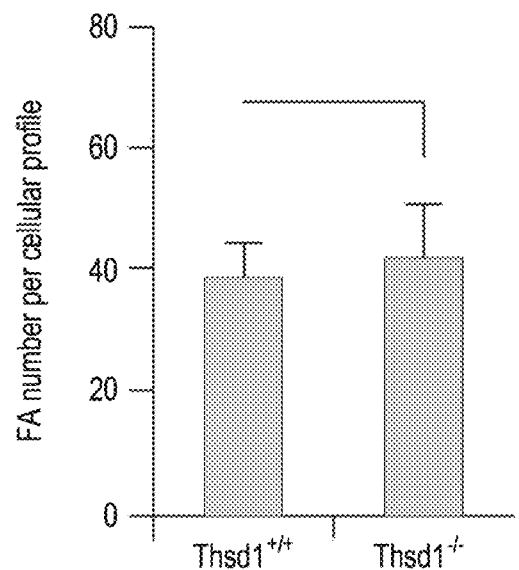

Collectively. FIGS. 8a-8c demonstrate that loss-of-function of Thsd1 reduces FA number in intimal endothelial cells in mouse circle of Willis. As shown in FIGS. 8a-8c, in control (FIG. 8a, panel a1) or Thsd1-deficient mice (FIG. 8a, panel a2). FAs in the endothelium of circle of Willis and morphology of endothelial cells were revealed by paxillin (green) and VE-cadherin (red), respectively, which were further quantified in (FIG. 8b). Arrows indicate the locations of FAs in enlarged pictures. (FIG. 8c) The FA number was not significantly affected in Thsd1-deficient primary smooth muscle cells from circle of Willis. **=p<0.01. n.s.: not significant. Scale bar: 1 μm. In conclusion. Focal adhesion is compromised in Thsd1-deficient mice.

Collectively, the data from two distinct animal models, a mammalian and a non-mammalian animal model demonstrates that autophagy plays a role in THSD1-mediated focal adhesion stability and IA formation.

Example 4: Treatment of Subjects with Unruptured Intracranial Aneurysm Bulges In-Vivo with an Inhibitor of Autophagosome Biogenesis In-Vivo Zebrafish Model Vertepofin is dissolved in DMSO as 10 mM. The working concentration of vertepofin is 10 uM. Both control and Thsd1-deficient zebrafish will be treated at 1 dpf (day post fertilization) for 24 hours and hemorrhage incidence will be counted at 2 dpf (n>80 for each genotype X treatment). The zebrafish model is well known for its case-of-use in drug evaluation in vivo as drugs can be directly added to embryo water. Similarly, we will treat Thsd1-deficient zebrafish with other two drugs including chloroquine and clomipramine. The working concentration for each is 100 uM and 10 uM, respectively.

Figure 9C:
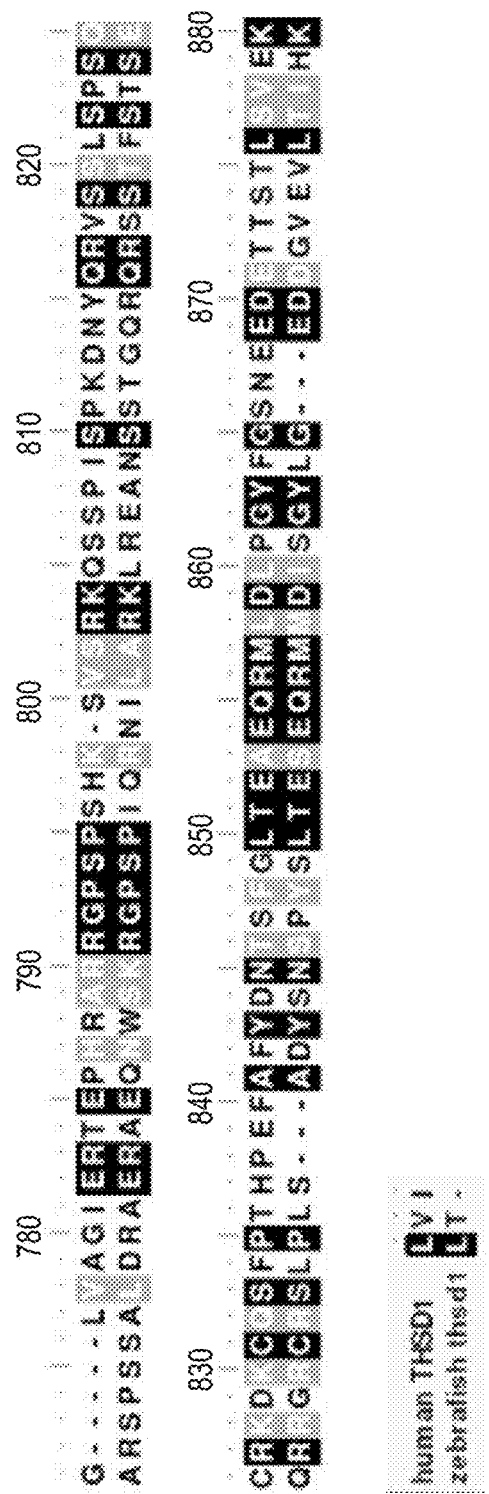
Figure 10:
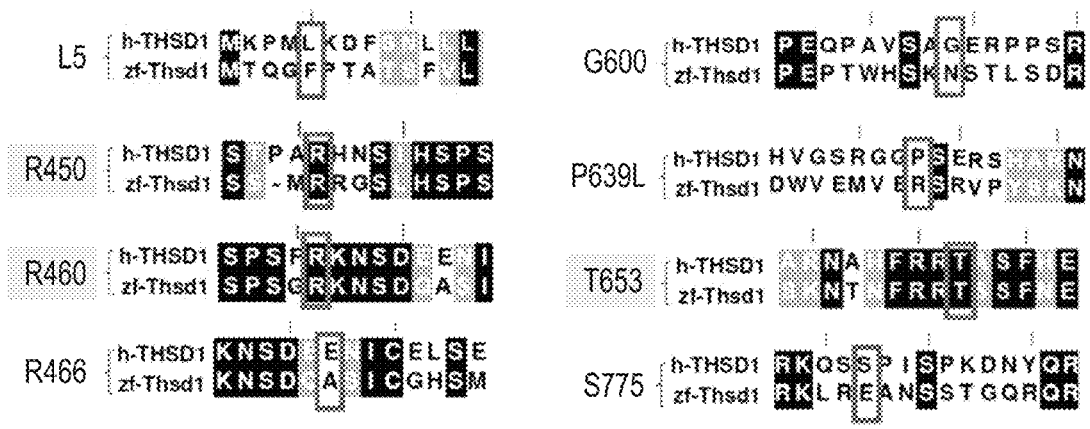
FIG. 10 is a sequence alignment illustrating three rare variants of thsd1 conserved between humans and fish.

Example 5: Genetic Engineering of Non-Human Animal Models Encoding Distinct THSD1 Rare Variants for In-Vivo Assessment of Efficacy of Various Autophagy Inhibitors Identified Conserved Sequences Suitable for Assessing Cross Species Efficacies of Treatments:

A protein alignment between human and zebrafish THSD1 was performed. See FIG. 9 illustrates the result of the alignment with black color indicating identical amino acids and the grey color indicating similar amino acids between humans and zebra fish. The alignment underscored that three rare variants of THSD1 identified in the aforementioned examples were conserved between human and zebrafish. The conserved amino acids include R450, R460 and T653. See, e.g., FIG. 10. The conserved amino acids were used as a rational for generating animal models of the human condition. The following constructs were generated:

TABLE 5

| 1 | pCS2 + zf-thsd1-WT-CT2FLAG (for full rescue, positive control) |
| 2 | pCS2 + zf-thsd1-R449X-CT2FLAG (corresponding to R450X in human) |
| 3 | pCS2 + zf-thsd1-R459W-CT2FLAG (corresponding to R460W in human) |
| 4 | pCS2 + zf-thsd1-T665I-CT2FLAG (corresponding to T653I in human) |

Mutations R449X, R459W and T665I were found to be conserved between human and zebrafish. Subsequently, the nucleic acid constructs encoding these sequences were introduced into zebrafish thsd1 by PCR mutagenesis. Specifically, the thsd1 variant or the WT sequence was subcloned into pCS2+ zebrafish vector for expression. These constructs were used as tools to study cerebrovascular integrity mediated by thsd1 WT and rare variants in the zebrafish animal model selected to model a human condition.

In-Vivo Zebrafish Model

Figure 11:
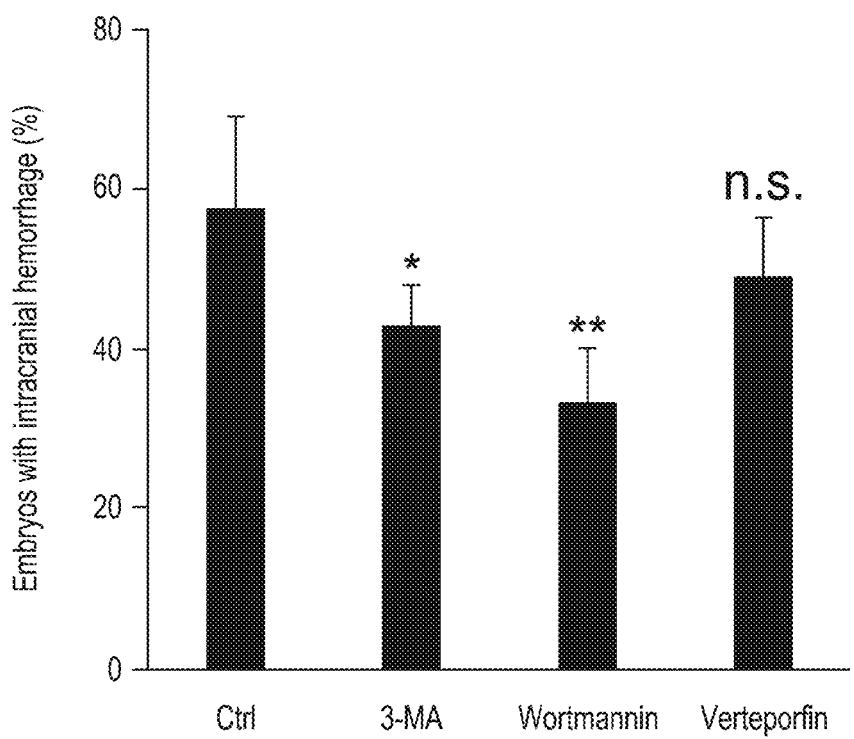
FIG. 11 is a graph charting the results of treatment of a model organism with conserved sequences demonstrating that autophagy inhibitors rescued intracranial hemorrhage. Three exemplary inhibitors disclosed on this chart include 3-MA, Wortmannin, and Verteporfin.

To test the hypothesis that autophagy inhibition could treat intracranial hemorrhage in-vivo 80-120 different zebrafish animals genetically engineered as described in Table 5 were treated with three distinct autophagy inhibitors, namely, 3-MA, wortmannin, or verteporfin. Control (DMSO) or other known autophagy inhibitors including 3-MA (10 mM), wortmannin (50 nM), and verteporfin (1 uM) were added to embryo water at 1 dpf for 24 hours. All embryos were injected by thsd1-MO and the hemorrhagic incidence was counted under microscope. For each injection, around 80-120 embryos were injected. *p<0.05, p<0.01, n.s. means not significant. See FIG. 11**.

The data demonstrates a body of work that first identified and studied a large number of human families with a disease. After significant effort in contacting individuals and sequencing the families shown in FIG. 1A, the present disclosure first identified THSD1 as a gene associated with sub-cranial hemorrhage. In specific cases, a single codon substitution was identified as responsible for the phenotype L5F, R460W, E466G, G600E, P639L, T653I, or S775P. The inventors developed a plethora of nucleic acid constructs, cell lines, and transgenic animal models to study the condition. Subsequently, a detailed characterization of molecular pathways whose transcription was disturbed in the disease condition was used to identify potential druggable targets and pathways for treatment. One such pathway was autophagy. Three distinct autophagy inhibitors were tested including 3-MA (10 mM), wortmannin (50 nM), and verteporfin (1 uM) and its ability to treat subjects, particularly its ability to treat subjects susceptible to an aneurism rupture was tested by counting the hemorrhagic incidence under the microscope on an animal model. The results illustrate that autophagy inhibition provides a treatment for modulating the rupture of an aneurysm in vivo.

Example 6: Kits

The disclosure contemplates kits comprising an autophagy inhibitor selected from the group consisting of wortmannin, chloroquine, clomipramine, 3-Methyladenine, Bafilomycin A1, Pepstatin A, and Pepstatin E-64-d and instructions for use of the same in the treatment of a condition disclosure herein. Specifically, the disclosure contemplates use of these drugs in treating an intracranial aneurysm.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 6.

We claim:

1. A method for treating a human subject at risk of suffering from an intracranial aneurysm comprising administering to said human subject a therapeutically effective dose of an autophagy inhibitor, wherein the autophagy inhibitor is selected from the group consisting of wortmannin, chloroquine, clomipramine, 3-Methyladenine, Bafilomycin A1, Pepstatin A, and Pepstatin E-64-d, wherein the human subject carries a variant affecting the expression of a Thrombospondin Type 1 Domain Containing 1 (THSD1) gene.

2. The method of claim 1, wherein the autophagy inhibitor is wortmannin.

3. The method of claim 1, wherein the autophagy inhibitor is chloroquine.

4. The method of claim 1, wherein the autophagy inhibitor is clomipramine.

5. The method of claim 1, wherein the autophagy inhibitor is 3-Methyladenine.

6. The method of claim 1, wherein the autophagy inhibitor is Bafilomycin A1.

7. The method of claim 1, wherein the autophagy inhibitor is Pepstatin A.

8. The method of claim 1, wherein the autophagy inhibitor is Pepstatin E-64-d.

9. The method of claim 1, wherein the variant is in a coding region of the Thrombospondin Type 1 Domain Containing 1 (THSD1) gene.

10. The method of claim 1, wherein the variant is in a control sequence of a non-coding region of the Thrombospondin Type 1 Domain Containing 1 (THSD1) gene.

11. The method of claim 1, wherein the variant in the THSD1 gene is a single codon substitution in at least one THSD1 allele.

12. The method of claim 1, wherein the single codon substitution is L5F, R460W, E466G, G600E, P639L, T653I, or S775P.

13. The method of claim 1, wherein the therapeutically effective dose of the autophagy inhibitor is administered systemically.

14. The method of claim 13, wherein systemic administration comprises: (i) intravenous, (ii) intra-arterial; (iii) subcutaneous; or (iv) intraperitoneal.

15. The method of claim 1, wherein the therapeutically effective dose of the autophagy inhibitor is administered locally.

16. The method of claim 15, wherein local administration includes, but is not limited to, (i) intracranial; (ii) intra-ocular; (iii) intra-nasal; (iv) intrathecal or (v) intra-vascular.

* * * * *